United States Patent [19]

Hashimoto et al.

[11] 4,369,312

[45] Jan. 18, 1983

[54] METHOD OF PRODUCING OXO-CONTAINING AZETIDINONE COMPOUNDS

[75] Inventors: Masashi Hashimoto, Takarazuka; Matsuhiko Aratani, Suita; Daijiro Hagiwara, Moriguchi; Kozo Sawada, Toyonaka; Tetsuo Onami, Fukushima, all of Japan

[73] Assignee: Fujisawa Pharmaceutical Co., Ltd., Osaka, Japan

[21] Appl. No.: 279,546

[22] Filed: Jul. 1, 1981

[30] Foreign Application Priority Data

Jul. 4, 1980 [JP] Japan ................................. 55-92059
Sep. 8, 1980 [JP] Japan ................................. 55-124799

[51] Int. Cl.³ .................. C07D 501/04; C07D 499/00
[52] U.S. Cl. ............................... 544/16; 260/245.2 R; 260/245.3; 544/22; 544/26; 544/28; 544/30
[58] Field of Search ................ 260/245.2 R; 424/270, 424/246; 544/16, 22, 26, 28, 30

[56] References Cited

U.S. PATENT DOCUMENTS 4,020,057  4/1977  Gleason ..................... 260/243 C
4,053,468 10/1977  Hulden ....................... 544/30

FOREIGN PATENT DOCUMENTS 2224131 10/1974 France .
2250758  6/1975 France .
2340322  9/1977 France .
2342293  9/1977 France .

OTHER PUBLICATIONS

J. C. Sheehan et al., The Journal of Organic Chemistry, vol. 42, (No. 6), p. 1012.
J. C. Sheehan et al., The Journal of Organic Chemistry, vol. 38, (No. 18), p. 3227.

Primary Examiner—Nicholas S. Rizzo
Attorney, Agent, or Firm—Oblon, Fisher, Spivak, McClelland & Maier

[57] ABSTRACT

This invention relates to a novel method of producing oxo-containing azetidinone compounds, or salts thereof, or hydrates thereof, said compounds having utility as antimicrobial agents and as intermediates for the synthesis of other azetidinone compounds having antimicrobial activity.

2 Claims, No Drawings

METHOD OF PRODUCING OXO-CONTAINING AZETIDINONE COMPOUNDS

This invention relates to novel oxo-containing azetidinone compounds or a salt thereof or a hydrate thereof, and to a novel method of producing oxo-containing azetidinone compounds or a salt thereof or a hydrate thereof.

More particularly, this invention relates to novel oxo-containing azetidinone compounds or a salt thereof or a hydrate thereof, which are useful as antimicrobial agent and are also of value as intermediates for the synthesis of another azetidinone compounds having antimicrobial activity, and to a novel method of producing oxo-containing azetidinone compounds or a salt thereof or a hydrate thereof.

With regard to the state of the prior arts, methods for producing oxo-containing azetidinone compounds from azetidinone compounds having a free or substituted amino group have been described in the literature cited below, but none of these methods are satisfactory for commercial purposes in view of the lack of yield data or the prolonged reaction that is required.

(1) Japan Published Unexamined Patent Application (Kokai tokkyo koho) No. 102296/1977

(2) J. C. Sheehan: Journal of Organic Chemistry, Volume 42, Page 1012 (1977)

An intensive study undertaken by the inventors of the present invention has resulted in the development of novel oxo-containing azetidinone compounds which are of value as intermediates for the synthesis of azetidinone compounds having antimicrobial activity and a novel method of producing oxo-containing azetidinone compounds.

The novel oxo-containing azetidinone compounds according to this invention are represented by the following general formula:

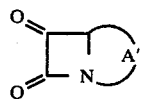

wherein A' is a group of the formula:

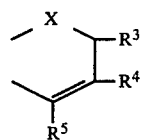

in which
  $R^3$ is hydrogen or alkyl,
  $R^4$ is hydrogen, halogen, alkyl, alkoxy, acyloxymethyl or substituted or unsubstituted heterocyclic-thiomethyl,
  $R^5$ is carboxy or protected carboxy, and
  X is —S— or —O—,
provided that when A' is a group of the formula:

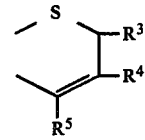

then
  $R^4$ is hydrogen, halogen, alkoxy or carbamoyloxymethyl protected by an amino-protecting group, and
  $R^3$ and $R^5$ are each as defined above.

The oxo-containing azetidinone compounds or a salt thereof of this invention can be produced by the processes depicted below.

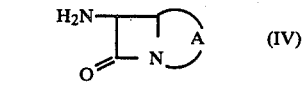

or a reactive derivative at the amino group thereof or a salt thereof

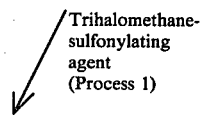

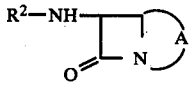

or a salt thereof

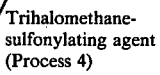
or a salt thereof (I) Base
(II) Hydrolysis
(Process 5)

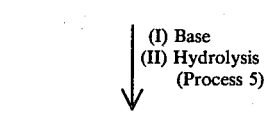

(I)
or a salt thereof
or a hydrate thereof

In the above formulas,
  $R^1$ is trihalomethanesulfonyl,
  $R^2$ is acyl, and
  A is a group of the formula:

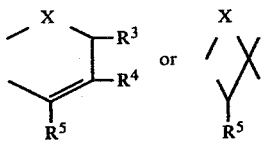

in which
R³ is hydrogen or alkyl;
R⁴ is hydrogen, halogen, alkyl, alkoxy, acyloxymethyl, or substituted or unsubstituted heterocyclic-thiomethyl;
R⁵ is carboxy or protected carboxy;
X is —S— or —O—.

The salt of the oxo-containing azetidinone compounds (I) and of the starting materials (III), (III') and (II) mentioned in connection with Methods 2 to 4 may, for example, be inorganic salts such as alkali metal salts, e.g. sodium salt, potassium salt, etc., alkaline earth metal salts, e.g. calcium salt, magnesium salt, etc., ammonium salts, etc. and organic salts such as organic base salts, e.g. trimethylamine, triethylamine, pyridine, picoline, dicyclohexylamine, N,N'-dibenzylethylenediamine, N-methylglucamine, diethanolamine, triethanolamine, tris(hydroxymethylamino)methane, etc.

The salt of the starting material (IV) in Method 1 may for example be, in addition to the abovementioned base salts, salts with inorganic acids such as hydrochloride, hydrobromide, sulfate, etc. and salts with organic acids such as formate, acetate, methanesulfonate, p-toluenesulfonate, etc.

The definitions of the object compounds (I) of this invention and of the starting materials (II), (III), (III') and (IV) used in Methods 1 to 5 are hereinafter given and explained in detail.

Unless otherwise indicated, the term "lower" means a group containing 1 to 6 carbon atoms and the term "higher" means a group containing 7 to 18 carbon atoms.

Suitable "trihalomethanesulfonyl" for $R^1$ may be trifluoromethanesulfonyl, etc.

The "acyl" for $R^2$ includes aliphatic acyl groups, acyl groups containing an aromatic ring and acyl groups containing a heterocyclic ring.

Suitable acyl groups thus defined may be: aliphatic acyl groups such as lower or higher alkanoyl groups (e.g. formyl, acetyl, hexanoyl, heptanoyl, stearoyl, etc.), lower or higher alkoxycarbonyl groups (e.g. methoxycarbonyl, ethoxycarbonyl, tert-butoxycarbonyl, tert-pentyloxycarbonyl, heptyloxycarbonyl, octyloxycarbonyl, etc.), lower or higher alkanesulfonyl groups (e.g. methanesulfonyl, ethanesulfonyl, octanesulfonyl, etc.), carbamoyl, carbamoyl protected by an amino-protective group such as mono-, di- or trihaloalkanoyl (e.g. chloroacetyl, dichloroacetyl, trichloroacetyl, etc.), and the like;

aromatic acyl groups such as aroyl (e.g. benzoyl, toluoyl, naphthoyl), ar(lower)alkanoyl groups, for example, phenyl(lower)alkanoyl (e.g. phenylacetyl, phenylpropionyl, etc.), aryloxycarbonyl (e.g. phenoxycarbonyl, naphthyloxycarbonyl, etc.), aryloxy(lower)alkanoyl, for example, phenoxy(lower)alkanoyl (e.g. phenoxyacetyl, phenoxypropionyl, etc.), arylglyoxyloyl (e.g. phenylglyoxyloyl, naphthylglyoxyloyl, etc.), arenesulfonyl (e.g. benzenesulfonyl, p-toluenesulfonyl, etc.), and the like; and heterocyclic acyl groups such as heterocyclecarbonyl (e.g. thenoyl, furoyl, etc.), heterocyclic(lower)al-kanoyl (e.g. thienylacetyl, furylacetyl, etc.), heterocyclic-glyoxyloyl (e.g. thienylglyoxyloyl, furylglyoxyloyl, etc.), and the like. In more detail, the heterocyclic moieties of said heterocycle-carbonyl, heterocyclic-(lower)alkanoyl and heterocyclic-glyoxyloyl groups include saturated or unsaturated, monocyclic or polycyclic groups containing at least one hetero-atom such as oxygen, sulfur and nitrogen atoms.

Preferred example of such heterocyclic moieties may be unsaturated 3- to 8- (preferably 5- or 6-) membered monocyclic groups containing 1 to 2 sulfur atoms (e.g. thienyl, dihydrothiinyl, etc.) and unsaturated 3- to 8- (preferably 5- or 6-) membered monocyclic groups containing oxygen (e.g. furyl, etc.), and the like.

The above-mentioned acyl groups may optionally have 1 to 5 appropriate substituents which may be the same or different. Suitable examples of such substituents include lower alkyl (e.g. methyl, ethyl, etc.), lower alkoxy (e.g. methoxy, ethoxy, propoxy, etc.), lower alkylthio (e.g. methylthio, ethylthio, etc.) lower alkylamino (e.g. methylamino, etc.), cyclo(lower)alkyl (e.g. cyclopentyl, cyclohexyl, etc.) cyclo(lower)alkenyl (e.g. cyclohexenyl, cyclohexadienyl, etc.), halogens (e.g. fluoro, chloro, bromo, etc.), amino, cyano, nitro, carboxy, protected carboxy (which is fully described hereinafter), sulfo, sulfamoyl, imino, oxo, amino(lower)alkyl (e.g. aminomethyl, aminoethyl, etc.), and the like.

Preferred examples of thus-defined acyl groups for $R^2$ may be trihalomethanesulfonyl and lower alkanoyl groups.

Suitable "alkyl" for $R^3$ and $R^4$ may be lower and higher alkyl groups such as methyl, ethyl, propyl, isopropyl, butyl, isobutyl, tert-butyl, pentyl, neopentyl, hexyl, octyl, etc. Preferred embodiment thereof may be lower alkyl group, and more preferred one is $C_1$–$C_3$ alkyl.

Suitable "halogen" for $R^4$ may be chloro, bromo or iodo.

Suitable "alkoxy" for $R^4$ may be lower and higher alkoxy groups such as methoxy, ethoxy, propoxy, isopropoxy, butoxy, isobutoxy, tert-butoxy, pentyloxy, neopentyloxy, hexyloxy, octyloxy, etc. Preferred embodiment thereof may be lower alkoxy group and, more preferred one is $C_1$ to $C_3$ alkoxy group.

The acyl moiety of "acyloxymethyl" for $R^4$ includes aliphatic acyl, acyl containing aromatic ring and acyl containing heterocyclic ring.

Suitable examples of such acyl may be those mentioned for $R^2$ and preferred embodiment thereof may be lower alkanoyl group and carbamoyl group protected by amino-protecting group, and more preferred one is $C_1$ to $C_3$ alkanoyl group and trihalo(lower)alkanoylcarbamoyl group.

The heterocyclic moiety of "substituted or unsubstituted heterocyclic-thiomethyl" for $R^4$ may be saturated or unsaturated monocyclic or polycyclic groups containing at least one hetero-atom such as oxygen, sulfur and nitrogen atoms.

Preferred heterocyclic moieties may be:
unsaturated 3- to 8-membered (preferably 5- or 6-membered) monocyclic heterocyclic groups containing 1 to 4 nitrogen atoms [e.g. pyrrolyl, pyrrolinyl, imidazolyl, pyrazolyl, pyridyl and N-oxide thereof, dihydropyridyl, pyrimidinyl, pyrazinyl, pyradazinyl, etc., triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.], saturated 3- to 8-membered (preferably 5- or 6-membered) monocyclic heterocyclic groups containing 1 to 4 nitrogen atoms (e.g. pyrrolidinyl, imidazolidinyl, piperidino, piperazinyl, etc.), unsaturated fused heterocyclic groups containing 1 to 4 nitrogen atoms (e.g. indolyl, isoindolyl, indolidinyl, benzimidazolyl, quinolyl, isoquinolyl, indazolyl, benzotriazolyl, etc.), unsaturated 3- to 8-membered (preferably 5- or 6-membered) monocyclic heterocyclic groups containing 1 to 2 oxygen atoms and 1 to 3 nitrogen atoms [e.g. oxazolyl, isoxazolyl, oxadiazolyl (e.g. 1,2,4-oxadiazolyl, 1,3,4-oxadiazolyl, 1,2,5-oxadiazolyl, etc.)], saturated 3- to 8-membered (preferably 5- or 6-membered) monocyclic heterocyclic groups containing 1 to 2 oxygen atoms and 1 to 3 nitrogen atoms (e.g. morpholinyl, sydnonyl, etc.), unsaturated fused heterocyclic groups containing 1 to 2 oxygen atoms and 1 to 3 nitrogen atoms (e.g. benzoxazolyl, benzoxadiazolyl, etc.), unsaturated 3- to 8-membered (preferably 5- or 6-membered) monocyclic heterocyclic groups containing 1 or 2 sulfur atoms and 1 to 3 nitrogen atoms [e.g. thiazolyl, isothiazolyl, thiadiazolyl, (e.g. 1,2,3-thiadiazolyl, 1,2,4-thiadiazolyl, 1,3,4-thiadiazolyl, 1,2,5-thiadiazolyl, etc.), dihydrothiazinyl, etc.], saturated 3- to 8-membered (preferably 5- or 6-membered) monocyclic heterocyclic groups containing 1 or 2 sulfur atoms and 1 to 3 nitrogen atoms (e.g. thiazolidinyl, etc.), unsaturated 3- to 8-membered (preferably 5- or 6-membered) monocyclic heterocyclic groups containing 1 to 2 sulfur atoms (e.g. thienyl, dihydrodithiinyl, etc.), unsaturated fused heterocyclic groups containing 1 to 2 sulfur atoms and 1 to 3 nitrogen atoms (e.g. benzothiazolyl, benzothiadiazolyl, etc.), unsaturated 3- to 8-membered (preferably 5- or 6-membered) monocyclic heterocyclic groups containing an oxygen atom (e.g. furyl, etc.), unsaturated 3- to 8-membered (preferably 5- or 6-membered) monocyclic heterocyclic groups containing an oxygen atom and 1 to 2 sulfur atoms (e.g. dihydroxathiinyl, etc.), unsaturated fused heterocyclic groups containing 1 to 2 sulfur atoms (e.g. benzothienyl, benzodithiinyl, etc.), unsaturated fused heterocyclic groups containing an oxygen atom and 1 to 2 sulfur atoms (e.g. benzoxathiinyl, etc.), and so on.

The heterocyclic groups thus defined may optionally have 1 to 5 appropriate substituents which are the same or different.

Suitable example of such substituents may be lower alkyl groups (e.g. methyl, ethyl, etc.), lower alkoxy groups (e.g. methoxy, ethoxy, propoxy, etc.), lower alkylthio (e.g. methylthio, ethylthio, etc.), lower alkylamino (e.g. methylamino, etc.), cyclo(lower)alkyl (e.g. cyclopentyl, cyclohexyl, etc.), cyclo(lower)alkenyl, (e.g. cyclohexenyl, cyclohexadienyl, etc.), hydroxy, halogen (e.g. chloro, bromo, etc.), amino, cyano, nitro, carboxy, protected carboxy (which is fully described hereinafter), and the like.

Preferred embodiment of the heterocyclic groups may be unsaturated 5- or 6-membered monocyclic heterocyclic group containing 1 to 2 sulfur atoms and 1 to 3 nitrogen atoms, and one containing 1 to 4 nitrogen atom(s), which are optionally substituted by lower alkyl. More preferred one is thiadiazolyl and lower alkyl-substituted tetrazolyl.

Suitable "protected carboxy" for $R^5$ includes carboxy groups protected by appropriate protective groups which are normally used for the protection of carboxy groups in the 4- and 3-positions of cephalosporins and pencillins, respectively, and such protected carboxy may be esterified carboxy.

Suitable ester moiety of the aforementioned esterified carboxy group includes lower alkyl esters (e.g. methyl ester, ethyl ester, propyl ester, isopropyl ester, butyl ester, isobutyl ester, tertbutyl ester, pentyl ester, tertpentyl ester, hexyl ester, etc.), lower cycloalkyl(lower)alkyl esters (e.g. 1-cyclopropylethyl ester, etc.), lower alkenyl esters (e.g. vinyl ester, allyl ester, etc.), lower alkynyl esters (e.g. ethynyl ester, propynyl ester, etc.), lower alkoxyalkyl esters (e.g. methoxymethyl ester, ethoxymethyl ester, isopropoxymethyl ester, 1-methoxyethyl ester, 1-ethoxyethyl ester, etc.), lower alkylthioalkyl esters (e.g. methylthiomethyl ester, ethylthiomethyl ester, ethylthioethyl ester, isopropylthiomethyl ester, etc.), mono- (or di- or tri-) halo(lower)alkyl esters (e.g. 2-iodoethyl ester, 2,2,2-trichloroethyl ester, etc.), lower alkanoyloxy(lower)alkyl esters (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.), lower alkanesulfonyl(lower)alkyl ester (e.g. mesylmethyl ester, 2-mesylethyl ester, etc.), ar(lower)alkyl esters such as phenyl(lower)alkyl esters which may optionally have 1 to 4 appropriate substituents, for example, nitro, hydroxy, lower alkoxy, etc. [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, etc.], aryl esters such as substituted or unsubstituted phenyl esters which may optionally have one or more substituents such as halogen, lower alkoxy, etc. (e.g. phenyl ester, tolyl ester, tert-butylphenyl ester, xylyl ester, mesityl ester, cumenyl ester, 4-chlorophenyl ester, 4-methoxyphenyl ester, etc.), tri(lower)alkylsilyl esters (e.g. trimethylsilyl ester, etc.), and lower alkylthio esters (e.g. methylthio ester, ethylthio ester, etc.).

The methods for producing the object compound (I) in accordance with this invention are described in detail below.

(1) Method 1:

The compound (III) or a salt thereof can be produced by reacting a compound (IV) or a reactive derivative at the amino group thereof or a salt thereof with a trihalomethanesulfonylating agent.

While the starting material compound (IV) used for this reaction includes novel as well as known compounds, these novel compounds can be produced either by a method analogous to the method for synthesis of the known compounds or by a conventional method.

The reactive derivative at the amino group of compound (IV) includes the silyl derivatives which are obtainable by reacting the compound (IV) with a silyl compound such as bis(trimethylsilyl)acetamide, trimethylsilylacetamide, etc., isocyanates, isothiocyanates, and the Schiff bases, inclusive of their enamine-type tautomers, which are obtainable by reaction of the amino group of the compound (IV) with an aldehyde such as acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthaldehyde, furfural, thiophenecarbaldehyde, etc. or a ketone compound such as acetone, methyl ethyl ketone, methyl isobutyl ketone, acethylacetone, ethyl acetoacetate, etc.

The trihalomethanesulfonylating agent used for this reaction includes trihalomethanesulfonic acid and its reactive derivatives such as the acid halide or acid anhydride thereof. Preferred examples thereof are the acid chloride, acid bromide and symmetric acid anhydride.

This reaction is desirably conducted in the presence of a base. Suitable examples of the base include inorganic or organic bases such as alkali metal hydrides (e.g. sodium hydride, etc.), alkaline earth metal hydrides (e.g. calcium hydride, etc.), alkali metal hydroxides (e.g. sodium hydroxide, potassium hydroxide, etc.), alkali metal carbonates (e.g. sodium carbonate, potassium carbonate, etc.), alkali metal bicarbonates (e.g. sodium bicarbonate, potassium bicarbonate, etc.), alkali metal alkoxides (e.g. sodium methoxide, sodium ethoxide, potassium tert-butoxide, etc.), tertiary amines such as trialkylamines (e.g. triethylamine, etc.), etc., secondary amines such as N-alkylarylamines (e.g. N-methylaniline, N-ethylaniline, etc.), N-alkylaralkylamines (e.g. N-methylbenzylamine, N-ethylbenzylamine, etc.), etc., N-alkylmorpholine compounds (e.g. N-methylmorpholine, etc.), pyridine compounds such as pyridine, lutidine, picoline, 4-(N,N-dialkylamino)pyridine [e.g. 4-(N,N-dimethylamino)pyridine, etc.], diazabicyclo compounds (e.g. 1,5-diazabicyclo[4,3,0]-5-nonene, 1,5-diazabicyclo[5,4,0]-5-undecene, 1,4-diazabicyclo[2,2,2]octane, etc.), quaternary ammonium salts (e.g. Triton B, etc.) and so on.

When this reaction is carried out by using a free trihalomethanesulfonic acid or a salt thereof, the reaction is preferably conducted in the presence of a condensing agent such as carbodiimide compounds [e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], phosphorus compounds (e.g. ethyl polyphosphate, isopropyl polyphosphate, phosphoryl chloride, phosphorus pentachloride, etc.), thionyl chloride, oxalyl chloride, etc., and Vilsmeier reagents which are obtainable by reacting an amide compound (e.g. dimethylformamide, diethylacetamide, N-methylformamide, etc.) with a halogen compound (e.g. thionyl chloride, phosphoryl chloride, phosgene, etc.).

This reaction is normally carried out in conventional solvents which will not interfere with the reaction such as methylene chloride, chloroform, tetrahydrofuran, dioxane, ethyl acetate, etc., or a mixture thereof.

While the reaction temperature is not critical, the reaction is normally conducted under mild conditions, i.e. under cooling to slightly warming.

(2) Method 2:

The compound (II) or a salt thereof can be produced by reacting the compound (III) or a salt thereof with an acylating agent.

The acylating agent for this reaction includes organic carboxylic acids, organic sulfonic acids and their reactive derivatives which are capable of introducing the acyl group for $R^2$.

Suitable examples of such reactive derivatives of acylating agent include, for example, acid halides, acid anhydrides, activated amides, activated esters, etc. Particularly preferred examples thereof are acid chloride, acid bromide, a mixed acid anhydride with substituted phosphoric acid (e.g. dialkylphosphoric acid, phenylphosphoric acid, diphenylphosphoric acid, dibenzylphosphoric acid, halogenated phosphoric acid, etc.), a mixed acid anhydride with dialkylphosphorous acid, a mixed acid anhydride with sulfurous acid, a mixed acid anhydride with thiosulfuric acid, a mixed acid anhydride with sulfuric acid, a mixed acid anhydride with alkylcarbonic acid (e.g. methylcarbonic acid, ethylcarbonic acid, etc.), a mixed acid anhydride with aliphatic carboxylic acid (e.g. pivalic acid, pentanoic acid, isopentanoic acid, 2-ethylbutanoic acid, trichloroacetic acid, etc.), a mixed acid anhydride with aromatic carboxylic acid (e.g. benzoic acid, etc.), and other mixed anhydrides, symmetric anhydrides, and so on.

Any one of these reactive derivatives is selected depending upon a kind of the compound (III) to be employed.

This reaction is conducted substantially in the same manner as Method 1 and, therefore, the foregoing explanation of the reaction mode (e.g. base, condensing agent, etc.), conditions (e.g. reaction solvent, temperature, etc.), etc. therein can apply equally to this Method 1.

(3) Method 3:

The compound (III') or a salt thereof can be produced by reacting the compound (IV) or a reactive derivative at the amino group thereof or a salt thereof with an acylating agent.

This reaction is carried out substantially in the same manner as Method 2 and, therefore, the acylating agent for this reaction are the same as these mentioned for Method 2. As to the reaction mode (e.g. base, condensing agent, etc.), reaction conditions (e.g. reaction solvent, temperature, etc.), etc. may be the same as those described for Method 1.

(4) Method 4:

The compound (II) or a salt thereof can be produced by reacting the compound (III') or a salt thereof with a trihalomethanesulfonylating agent.

This reaction is conducted substantially in the same manner as Method 1, and therefore, the explanation of trihalomethanesulfonylating agent, reaction mode (e.g. base, condensing agent, etc.), reaction conditions (e.g. reaction solvent, temperature, etc.), etc. for Method 1 can apply equally to this Method 1.

(5) Method 5:

The compound (I) or a salt thereof or a hydrate thereof can be produced by reacting the compound (II) or a salt thereof with a base and then subjecting to hydrolysis.

In this process, the reaction of the compound (II) or a salt thereof with a base in the first place yields a compound of the following structural formula:

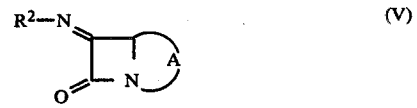

wherein $R^2$ and A are each as defined above, and subsequent hydrolysis of the resultant reaction product (V) gave the object compound (I).

Suitable examples of the base used for this reaction process may be the same as those given for Method 1, and preferred example thereof are tertiary amines such as trialkylamines, and diazabicyclo compounds.

The hydrolysis in this process is a usual hydrolysis used for conversion of a $>C\!=\!N-$ group to a $>C\!=\!O$ group, and such hydrolysis includes the hydrolysis in the presence of an acid such as an inorganic acid (e.g. hydrochloric acid, hydrobromic acid, sulfuric acid, phosphoric acid, etc.) or an organic acid (e.g. formic acid, acetic acid, propionic acid, benzenesulfonic acid, toluenesulfonic acid, etc.).

This reaction is usually carried out in a conventional solvent that will not interfere with the reaction such as those mentioned hereinbefore for Method 1.

While the reaction temperature is not critical, the reaction is normally conducted under mild conditions such as under cooling to warming.

In this reaction, the oxo-containing azetidinone compounds are occasionally obtained in the form of a hydrate having the following formula (I')

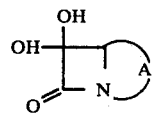

and such compounds are also included within the scope of this invention.

The object compounds (II), (III) and (III') in the above Methods 1 to 4 may be directly subjected to the next reaction without prior isolation.

The oxo-containing azetidinone compounds (I) and a salt thereof and a hydrate thereof possessing antimicrobial activities can be optionally transformed into more active antimicrobial agents by known reaction method(s), for example, the ones as shown in the following "literature", or the ones as shown in the following reaction schemes as "references".

Literature (1) J. C. Sheehan et. al.: Journal of Organic Chemistry, Volume 38, page 3227 (1973)

(2) J. C. Sheehan et. al.: Journal of Organic Chemistry, Volume 42, page 1012 (1977)

(3) Japan Published and Unexamined patent application (Kokai tokkyo koho) No. 5788/1977

References

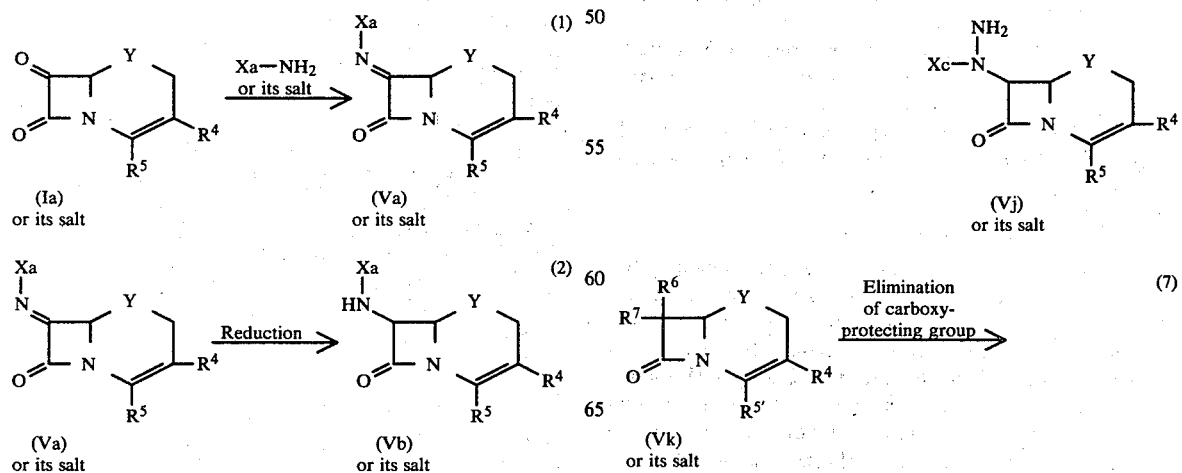

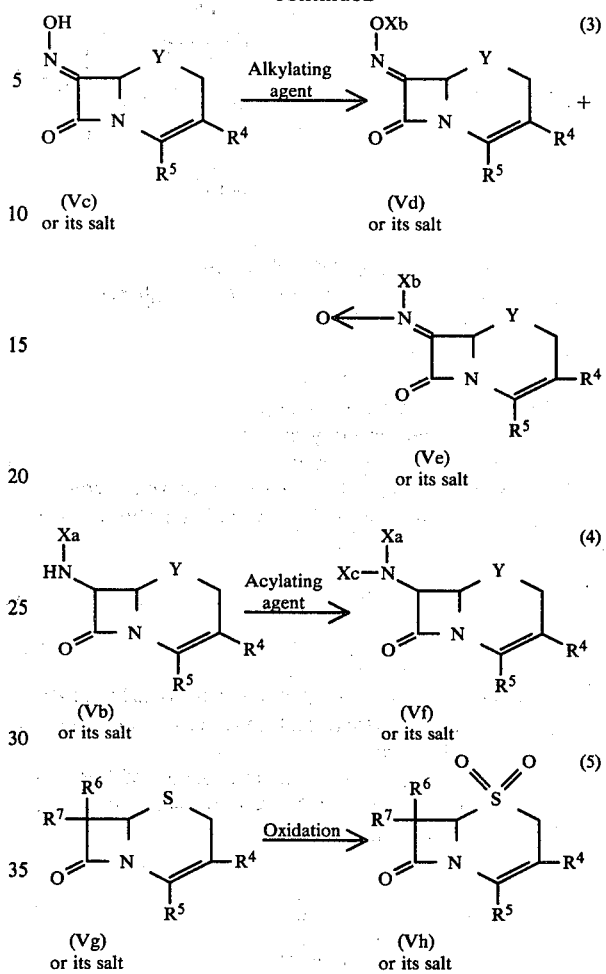

-continued

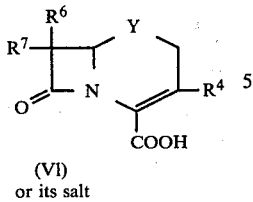

(VI) or its salt wherein

R⁴ and R⁵ are each as defined above,

Xa is hydroxy, lower alkoxy, ar(lower)alkoxy or a protected amino group,

Xb is lower alkyl,

Xc is acyl,

Xd is a protected amino group, $R^{5'}$ is a protected carboxy group,

Y is —S— or —SO₂—, and

R⁶ is hydrogen and R⁷ is a group of the formula: Xa—NH— in which Xa is as defined above, or a group of the formula:

in which Xc is as defined above, and Xe is hydroxy, lower alkoxy, ar(lower)alkoxy, amino or a protected amino group, or R⁶ and R⁷ are together to form a group of the formula: Xa-N= in which Xa is as defined above or a group of the formula:

in which Xb is as defined above.

Antimicrobial activities of some of the antimicrobial agents obtained from the object compounds (I) according to References (1) to (7) mentioned above are shown in the following.

Test: In vitro Antimicrobial Activity.

Test Compounds

No. 1 Sodium 7-[N-methoxy-2-(2-thienyl)acetamido]-cephalosporanate.

No. 2 7-[N-Methoxy-2-(2-thienyl)acetamido]-3-(1-methyl-1H-tetrazol-5-ylthiomethyl)-3-cephem-4-carboxylic acid.

No. 3 7-[N-Hydroxy-2-(2-thienyl)acetamido]-3-(1-methyl-1H-tetrazol-5-ylthiomethyl)-3-cephem-4-carboxylic acid.

Test Method

In vitro Antimicrobial activity was determined by the two-fold agar-plate dilution method as described below.

One loopful of an overnight culture of each test strain in Tripticase-soy broth (approximately 10⁸ viable cells per ml) was streaked on heart infusion agar (HI-agar) containing graded concentrations of antimicrobial agents, and the minimal inhibitory concentration (MIC) was expressed in term of µg/ml after incubation at 37° C. for 20 hours.

Test Results

| | MIC (µg/ml) | | |
| | Microorganisms | | |
| Test compounds | Staphylococcus aureus 209P JC-1 | Bacillus subtilis ATCC 6633 | Escherichia coli 31 |
| --- | --- | --- | --- |
| 1 | 6.25 | 0.78 | 6.25 |
| 2 | 3.13 | 0.78 | 1.56 |
| 3 | 6.25 | 3.13 | 6.25 |

The following examples are given for the purpose of illustrating this invention in more detail.

EXAMPLE 1

(1) A solution of benzhydryl 7-amino-3-(1-methyl-1H-tetrazol-5-ylthiomethyl)-3-cephem-4-carboxylate (3.96 g) in methylene chloride (60 ml) was cooled to −60° C., and then triethylamine (3.35 ml) and trifluoromethanesulfonic anhydride (4.71 ml) were added to the solution. The mixture was stirred at the same temperature for 1 hour at −50°∼−30° C. for 30 minutes, and then at −30°∼−10° C. for another 30 minutes. The reaction mixture was poured in a cold aqueous sodium chloride and extracted with a mixture of diethyl ether (250 ml) and ethyl acetate (50 ml). The extract was washed with an aqueous sodium chloride and dried over magnesium sulfate. The solvent was then distilled off. The resultant crystalline solid was washed with a solvent mixture of diisopropyl ether and hexane to give benzhydryl 7-[N,N-bis(trifluoromethanesulfonyl)amino]-3-(1-methyl-1H-tetrazol-5-ylthiomethyl)-3-cephem-4-carboxylate (5.40 g). Mp. 125°–127° C. (dec.)

I.R. (Nujol): 1800, 1720, 1240 cm⁻¹

N.M.R. δppm (CDCl₃): 3.84 (2H, ABq, J=14 Hz), 4.60 (2H, ABq, J=13 Hz), 5.14 (1H, d, J=5 Hz), 5.90 (1H, d, J=5 Hz), 7.07 (1H, s), 7.3–7.7 (10H, m)

(2) A solution of benzhydryl 7-amino-3-(1-methyl-1H-tetrazol-5-ylthiomethyl)-3-cephem-4-carboxylate (5.00 g) in methylene chloride (100 ml) was cooled to −65° C., and then triethylamine (1.55 ml) and trifluoromethanesulfonic anhydride (1.87 ml) were added to the solution. The mixture was stirred at the same temperature for 30 minutes. The reaction mixture was washed with an aqueous sodium chloride containing 1 N hydrochloric acid and an aqueous sodium chloride in that order, and dried over magnesium sulfate. The solvent was then distilled off. The resultant oil was crystallized from a solvent mixture of ethyl acetate and diethyl ether and collected by filtration to give benzhydryl 7-(N-trifluoromethanesulfonylamino)-3-(1-methyl-1H-tetrazol-5-ylthiomethyl)-3-cephem-4-carboxylate (4.90 g). Mp. 100°–105° C.

I.R. (Nujol): 1780, 1720, 1240 cm⁻¹

N.M.R. δppm (CDCl₃): 3.73 (2H, broad s), 3.80 (3H, s), 4.33 (2H, ABq, J=13 Hz), 5.00 (1H, d, J=5 Hz), 5.40 (1H, d, J=5 Hz), 6.93 (1H, s), 7.2–7.6 (10H, m)

The compound (1.00 g) obtained above was dissolved in methylene chloride (20 ml) and the solution was cooled to −60° C. To this solution were added triethylamine (0.32 g) and trifluoromethanesulfonic anhydride (0.90 g), and the mixture was stirred at the same temperature for 1 hour, and then at −50°∼−30° C. for another 1 hour. The reaction mixture was poured in an aqueous sodium chloride and extracted with ethyl acetate. The extract was washed with an aqueous sodium chloride and dried over magnesium sulfate. The solvent was then distilled off. The oily residue was crystallized from diisopropyl ether to give benzhydryl 7-[N,N-bis-(trifluoromethanesulfonyl)amino]-3-(1-methyl-1H-tetrazol-5-ylthiomethyl)-3-cephem-4-carboxylate (0.85 g).

I.R. (Nujol): 1800, 1720, 1240 cm$^{-1}$ (3) A solution of benzhydryl 7-[N,N-bis(trifluoromethanesulfonyl)amino]-3-(1-methyl-1H-tetrazol-5-ylthiomethyl)-3-cephem-4-carboxylate (1.27 g) in methylene chloride (15 ml) was cooled to $-60°$ C., and then triethylamine (0.408 ml) was added to the solution. The mixture was stirred at the same temperature for 1.5 hours. The reaction mixture was poured in a mixture of benzene and 0.1 N hydrochloric acid. The organic layer was washed with an aqueous sodium chloride and dried over magnesium sulfate. The solvent was then distilled off. The resultant oil was subjected to silica gel column chromatography, elution being carried out with a mixture of benzene and acetone (100:2-100:8, v/v). The active fractions were pooled and concentrated to dryness under reduced pressure to give an oil of benzhydryl 7-oxo-3-(1-methyl-1H-tetrazol-5-ylthiomethyl)-3-cephem-4-carboxylate (0.58 g).

I.R. (CHCl$_3$): 1820, 1780, 1720 cm$^{-1}$

N.M.R. δppm (CDCl$_3$): 3.76 (2H, broad s), 3.80 (3H, s), 4.34 (2H, ABq, J=14 Hz), 5.28 (1H, s), 7.00 (1H, s), 7.1-7.5 (10H, m)

EXAMPLE 2

(1) A solution of benzhydryl 7-aminocehalosporanate (1.71 g) in methylene chloride (20 ml) was cooled to $-65°$ C., and then triethylamine (1.06 g) and trifluoromethanesulfonic anhydride (2.80 g) were added to the solution. The reaction mixture was stirred, while its temperature was gradually increased to 0° C. over 2 hours. The solution was cooled to $-60°$ C., followed by addition of trifluoromethanesulfonic anhydride (0.57 g) and triethylamine (0.21 g), and the mixture was stirred, while its temperature was gradually increased to $-10°$ C. over 1 hour and 40 minutes. The reaction mixture was poured in a mixture of ethyl acetate and water, and then the organic layer was taken, washed with water and a saturated aqueous sodium chloride in that order, followed by drying over magnesium sulfate. The solvent was then distilled off to give benzhydryl 7-[N,N-bis(trifluoromethanesulfonyl)amino]cephalosporanate (2.49 g).

I.R. (CH$_2$Cl$_2$): 1810, 1750, 1220, 1160 cm$^{-1}$ (2) A solution of benzhydryl 7-aminocephalosporanate (1.0 g) in methylene chloride (15 ml) was cooled to $-60°$ C., and then triethylamine (0.277 g) and trifluoromethanesulfonic anhydride (0.708 g) were added to the solution in a nitrogen gas stream. The mixture was stirred at the same temperature for 10 minutes. The reaction mixture was poured in a mixture of ethyl acetate and dilute hydrochloric acid, and the organic layer was taken, washed with 1 N hydrochloric acid and an aqueous sodium chloride in that order, and dried over magnesium sulfate. The solvent was then distilled off. The resultant residue was subjected to silica gel (16 g) column chromatography, elution being carried out with a solvent mixture of methylene chloride and ethyl acetate (15:1, v/v). The active fractions were pooled and the solvent was distilled off to give benzhydryl 7-(N-trifluoromethanesulfonylamino)cephalosporanate (1.03 g).

I.R. (CH$_2$Cl$_2$): 3300, 1790, 1730, 1210 cm$^{-1}$

N.M.R. δppm (DMSO-d$_6$): 1.96 (3H, s), 3.64 (2H, m), 4.74 (2H, ABq, J=13 Hz), 5.15 (1H, d, J=4.5 Hz), 5.67 (1H, d, J=4.5 Hz), 6.89 (1H, s), 7.2-7.5 (10H, m)

The compound (1.40 g) thus obtained was dissolved in methylene chloride (20 ml) and the solution was cooled to $-60°$ C. After addition of triethylamine (0.264 g) and trifluoromethanesulfonic anhydride (0.669 g), the mixture was stirred, while its temperature was gradually increased to $-20°$ C. over 1 hour and 20 minutes, and then allowed to stand in a refrigerator overnight. The reaction mixture was concentrated to about one-third of the initial volume and the concentrate was poured in ethyl acetate. The solution was washed with 1 N hydrochloric acid, an aqueous sodium bicarbonate, water and an aqueous sodium chloride in that order, and then dried over magnesium sulfate. The solvent was distilled off and the resultant residue (1.38 g) was subjected to silica gel (25 g) column chromatography, elution being carried out with methylene chloride. The active fractions were pooled and the solvent was distilled off to give benzhydryl 7-[N,N-bis(trifluoromethanesulfonyl)amino]cephalosporanate (0.64 g).

I.R. (CH$_2$Cl$_2$): 1810, 1750, 1220, 1160 cm$^{-1}$

N.M.R. δppm (CDCl$_3$): 2.03 (3H, s), 3.50 (2H, ABq, J=16 Hz), 5.00 (1H, d, J=4 Hz), 5.10 (2H, ABq, J=14 Hz), 5.80 (1H, d, J=4 Hz), 6.93 (1H, s), 7.33 (10H, s)

(3) A solution of benzhydryl 7-[N,N-bis-trifluoromethanesulfonyl)amino]cephalosporanate (2.49 g) in methylene chloride (20 ml) was cooled to $-60°$ C., and then triethylamine (0.394 g) was added all at a time. The mixture was stirred at the same temperature for 40 minutes, followed by addition of triethylamine (0.073 g) at $-50°$ C. While stirring the mixture, the temperature was increased to $-35°$ C. over 30 minutes. The reaction mixture was poured in a mixture of ethyl acetate and dilute hydrochloric acid and the organic layer was taken, washed with dilute hydrochloric acid and a saturated aqueous sodium chloride in that order, and dried over magnesium sulfate. The resultant residue (2.22 g) was subjected to silica gel (22 g) column chromatography, elution being carried out with methylene chloride, and then a mixture of methylene chloride and ethyl acetate (10:1, v/v). The active fractions were pooled and the solvent was distilled off to give an oil of benzhydryl 7-oxocephalosporanate (1.40 g).

I.R. (CH$_2$Cl$_2$): 1830, 1790, 1740 cm$^{-1}$

N.M.R. δppm (CDCl$_3$): 2.00 (3H, s), 3.50 (2H, ABq, J=18 Hz), 4.93 (2H, ABq, J=14 Hz), 5.27 (1H, s), 7.00 (1H, s), 7.33 (10H, s)

EXAMPLE 3

(1) Benzyl 6-aminopenicillanate p-toluenesulfonate (478 mg) was added to a mixture of ethyl acetate and an aqueous sodium bicarbonate. The ethyl acetate layer was taken and the residual aqueous solution was extracted with ethyl acetate. The ethyl acetate layers were combined, washed with a saturated aqueous sodium chloride and dried over magnesium sulfate. The solvent was then distilled off. The resultant residue (320 mg) was dissolved in methylene chloride (6 ml), followed by addition of triethylamine (242 mg) and trifluoromethanesulfonic anhydride (795 mg) at $-60°$ C. While stirring the mixture, the reaction temperature was increased to 0° C. over 2.5 hours, and the stirring was further continued at 0° C. for 30 minutes. To the reaction mixture was added ethyl acetate, the mixture was washed with a dilute aqueous sodium bicarbonate, 1 N hydrochloric acid and a saturated aqueous sodium chloride in that order, and dried over magnesium sulfate. The solvent was then distilled off to give benzyl 6-[N,N-bis(trifluoromethanesulfonyl)amino]penicillanate (467 mg).

I.R. (Nujol): 1800, 1735, 1725 cm$^{-1}$

N.M.R. δppm (acetone-d$_6$): 1.50 (3H, s), 1.73 (3H, s), 4.52 (1H, s), 5.25 (2H, s), 5.45 (1H, d, J=3.5 Hz), 6.26 (1H, d, J=3.5 Hz), 7.38 (5H, s)

(2) Benzyl 6-[N,N-bis(trifluoromethanesulfonyl)amino]penicillanate (467 mg) was dissolved in methylene chloride (6 ml) and the solution was cooled to −60° C. To the solution was added triethylamine (71 mg) and the mixture was stirred for 30 minutes. After further addition of triethylamine (22 mg), the mixture was stirred for 10 minutes. The reaction mixture was added to a mixture of ethyl acetate and 1 N hydrochloric acid, and the organic layer was taken, washed with a saturated aqueous sodium chloride, and dried over magnesium sulfate. The solvent was then distilled off and the resultant residue (423 mg) was subjected to silica gel (4.5 g) column chromatography, elution being carried out with a solvent mixture of methylene chloride and ethyl acetate (9:1, v/v). The active fractions were pooled and the solvent was distilled off to give an oil of benzyl 6-oxopenicillanate (239 mg).

I.R. (CH$_2$Cl$_2$): 1830, 1780, 1735 cm$^{-1}$

N.M.R. δppm (CDCl$_3$): 1.48 (3H, s), 1.55 (3H, s), 4.82 (1H, s), 5.24 (2H, s), 5.79 (1H, s), 7.36 (5H, s)

EXAMPLE 4

A solution of benzhydryl 7-aminocephalosporanate (1.71 g) in methylene chloride (20 ml) was cooled to −60° C., followed by addition of triethylamine (1.29 ml) and trifluoromethanesulfonic anhydride (1.52 ml), and the reaction temperature was gradually increased to −8° C. with stirring the mixture over 2.5 hours. The reaction mixture was cooled to −60° C. and triethylamine (0.62 ml) was added, followed by stirring for another 50 minutes. During this stirring, the reaction temperature was gradually increased to −30° C. The reaction mixture was poured in a mixture of ethyl acetate and water, and the organic layer was taken, washed with 1 N hydrochloric acid and a saturated aqueous sodium chloride in that order, and dried over magnesium sulfate. The solvent was distilled off and the resultant residue (2.34 g) was subjected to silica gel (25 g) column chromatography, elution being carried out with methylene chloride, and then a solvent mixture of methylene chloride and acetone (19:1, v/v). The active fractions were pooled and concentrated to dryness under reduced pressure to give benzhydryl 7-oxocephalosporanate as a crude product (0.86 g).

I.R. (CH$_2$Cl$_2$): 1830, 1790, 1740 cm$^{-1}$

EXAMPLE 5

4-Nitrobenzyl 7-amino-3-methoxy-3-cephem-4-carboxylate, trifluoromethanesulfonic anhydride, triethylamine and hydrochloric acid were reacted in the same manners as those of Examples 1–4 to give 4-nitrobenzyl 7-oxo-3-methoxy-3-cephem-4-carboxylate (monohydrate). Mp. 115°–120° C. (dec.).

I.R. (Nujol): 1770, 1750 cm$^{-1}$

N.M.R. δppm (DMSO-d$_6$): 3.56 (2H, ABq, J=16 Hz), 3.77 (3H, s), 4.75 (1H, s), 5.33 (2H, s), 7.78 (2H, d, J=9 Hz), 8.33 (2H, d, J=9 Hz)

EXAMPLE 6

4-Nitrobenzyl 7-amino-3-chloro-3-cephem-4-carboxylate, trifluoromethanesulfonic anhydride, triethylamine and hydrochloric acid were reacted in the same manners as those of Examples 1–4 to give 4-nitrobenzyl 7-oxo-3-chloro-3-cephem-4-carboxylate (monohydrate). Mp. 105°–106° C. (dec.).

I.R. (Nujol): 1790, 1735 cm$^{-1}$

N.M.R. δppm (DMSO-d$_6$): 3.83 (2H, ABq, J=17 Hz), 4.97 (1H, s), 5.50 (2H, s), 7.75 (2H, d, J=9 Hz), 8.30 (2H, d, J=9 Hz)

EXAMPLE 7

4-Nitrobenzyl 7-amino-3-cephem-4-carboxylate, trifluoromethanesulfonic anhydride, triethylamine and hydrochloric acid were reacted in the same manners as those of Examples 1–4 to give 4-nitrobenzyl 7-oxo-3-cephem-4-carboxylate. Mp. 141°–142° C. (dec.).

I.R. (CH$_2$Cl$_2$): 1830, 1790, 1730, 1520 cm$^{-1}$

N.M.R. δppm (CDCl$_3$): 3.60 (2H, m), 5.29 (1H, s), 5.40 (2H, s), 6.69 (1H, dd, J=5 Hz, 6 Hz), 7.60, 8.19 (4H, ABq, J=8 Hz)

EXAMPLE 8

2,2,2-Trichloroethyl 7-amino-2-methyl-3-cephem-4-carboxylate, trifluoromethanesulfonic anhydride, triethylamine and hydrochloric acid were reacted in the same manners as those of Examples 1–4 to give 2,2,2-trichloroethyl 7-oxo-2-methyl-3-cephem-4-carboxylate. Mp. 98° C.

I.R. (CH$_2$Cl$_2$): 1820, 1780, 1730 cm$^{-1}$

N.M.R. δppm (CDCl$_3$): 1.52 (3H, d, J=7 Hz), 3.75 (1H, dq, J=6 Hz, 7 Hz), 4.93 (2H, s), 5.25 (1H, s), 6.79 (1H, d, J=6 Hz)

EXAMPLE 9

Benzyl 7-amino-1-oxadethia-3-cephem-4-carboxylate, trifluoromethanesulfonic anhydride, triethylamine and hydrochloric acid were reacted in the same manners as those of Examples 1–4 to give benzyl 7-oxo-1-oxadethia-3-cephem-4-carboxylate.

I.R. (CH$_2$Cl$_2$): 1820, 1780, 1720 cm$^{-1}$

N.M.R. δppm (CDCl$_3$): 4.66 (2H, m), 5.26 (1H, s), 5.33 (2H, s), 6.45 (1H, m), 7.37 (5H, s)

EXAMPLE 10

Benzhydryl 7-amino-3-[N-(2,2,2-trichloroacetyl)carbamoyloxymethyl]-3-cephem-4-carboxylate trifluoromethanesulfonic anhydride, triethylamine and hydrochloric acid were reacted in the same manners as those of Examples 1–4 to give benzhydryl 7-oxo-3-[N-(2,2,2-trichloroacetyl)carbamoyloxymethyl]-3-cephem-4-carboxylate.

I.R. (CH$_2$Cl$_2$): 3380, 1825 (shoulder), 1805, 1790, 1750 (shoulder), 1730 cm$^{-1}$ N.M.R. δppm (CDCl$_3$): 3.60 (2H, ABq, J=20 Hz), 5.15 (2H, ABq, J=14 Hz), 5.33 (1H, s), 7.10 (1H, s), 7.44 (10H, s), 8.73 (1H, broad s)

EXAMPLE 11

2,2,2-Trichloroethyl 7-amino-3-methyl-3-cephem-4-carboxylate, trifluoromethanesulfonic anhydride, triethylamine and hydrochloric acid were reacted in the same manners as those of Examples 1–4 to give 2,2,2-trichloroethyl 7-oxo-3-methyl-3-cephem-4-carboxylate.

I.R. (CH$_2$Cl$_2$): 1820, 1780, 1740 cm$^{-1}$

N.M.R. δppm (CDCl$_3$): 2.37 (3H, s), 3.50 (2H, ABq, J=18 Hz), 4.93 (2H, ABq, J=11 Hz), 5.38 (1H, s)

EXAMPLE 12

Benzhydryl 7-amino-3-(1,3,4-thiadiazol-2-ylthiomethyl)-3-cephem-4-carboxylate, trifluoromethanesulfonic anhydride, triethylamine and hydrochloric acid were reacted in the same manners as those of Examples 1–4 to give benzhydryl 7-oxo-3-(1,3,4-thiadiazol-2-ylthiomethyl)-3-cephem-4-carboxylate.

I.R. ($CHCl_3$): 1825, 1780, 1720, 1665 $cm^{-1}$

EXAMPLE 13

7-Aminocephalosporanic acid, trifluoromethanesulfonic anhydride, triethylamine and hydrochloric acid were reacted in the same manners as those of Examples 1–4 to give 7-oxocephalosporanic acid.

I.R. (Nujol): 3450-3150, 1835, 1780, 1735, 1710 (shoulder), 1640 $cm^{-1}$

EXAMPLE 14

A solution of benzyl 6-[N,N-bis(trifluoromethanesulfonyl)amino]penicillanate (0.80 g) in tetrahydrofuran (8 ml) was cooled to $-60°$ C., followed by addition of 1,5-diazabicyclo[5,4,0]undecene-5 (0.298 g), and the mixture was stirred at the same temperature for 30 minutes. To the reaction mixture was added p-toluenesulfonic acid (monohydrate) (0.32 g), and the mixture was stirred at $-52°$ C. for 10 minutes. The reaction mixture was poured in a mixture of ethyl acetate and water, and the organic layer was taken, washed with dilute hydrochloric acid and an aqueous sodium chloride, and dried over magnesium sulfate. The solvent was distilled off and carbon tetrachloride was added to the oily residue (0.67 g). The resultant precipitate was filtered off. The filtrate was concentrated and the concentrate was subjected to silica gel (6.5 g) column chromatography, elution being carried out with a mixture of methylene chloride and ethyl acetate (6:1, v/v). The active fractions were pooled and concentrated to dryness under reduced pressure to give benzyl 6-oxopencillanate as yellow oil (280 mg).

I.R. ($CH_2Cl_2$): 1830, 1780, 1735 $cm^{-1}$

EXAMPLE 15

(1) A solution of benzhydryl 7-(N-trifluoromethanesulfonylamino)cephalosporanate (290 mg) in methylene chloride (6 ml) was cooled to $-60°$ C., followed by addition of triethylamine (199 mg) and acetyl chloride (150 mg), and the mixture was stirred at $-40°$ C. for 2 hours. Ethyl acetate and ice-water were added to the reaction mixture, and the organic layer was taken, washed with water and an aqueous sodium chloride in that order, and dried over magnesium sulfate. The solvent was distilled off and the resultant residue (510 mg) was subjected to silica gel (3.5 g) column chromatography, elution being carried out with methylene chloride. The active fractions were pooled and the solvent was distilled off to give benzhydryl 7-(N-acetyl-N-trifluoromethanesulfonylamino)cephalosporanate (334 mg).

I.R. ($CH_2Cl_2$): 1800, 1740, 1215 $cm^{-1}$

N.M.R. δppm ($CDCl_3$): 2.02 (3H, s), 2.58 (3H, s), 3.36 (2H, ABq, J=16 Hz), 4.99 (1H, d, J=4.5 Hz), 5.06 (2H, ABq, J=13 Hz), 5.45 (1H, d, J=4.5 Hz), 6.92 (1H, s), 7.3 (10H, s)

EXAMPLE 16

In dimethylformamide (20 ml) are dissolved 2,2,2-trichloroethyl 3-methyl-7-oxo-3-cephem-4-carboxylate (3.63 g) and methoxyamine hydrochloride (2.63 g), followed by addition of pyridine (0.83 g) and methylene chloride (70 ml). The mixture is refluxed in a Dean-Stark trap packed with Molecular Sieve 3A for 2 hours. The reaction mixture is concentrated under reduced pressure and the residue is dissolved in ethyl acetate. This solution is washed with water, 1 N-HCl and aqueous sodium chloride in the order mentioned, dried over magnesium sulfate and concentrated under reduced pressure. The residual oil is subjected to silica gel (35 g) column chromatography and elution is carried out with methylene chloride. By the above procedure is obtained 2,2,2-trichloroethyl 7-methoxyimino-3-methyl-3-cephem-4-carboxylate as as oil (3.66 g).

IR($CH_2Cl_2$) 1780, 1740 $cm^{-1}$

NMR($CDCl_3$)δ 2.22 (s, 3H), 3.38 (ABq, J=18 Hz, 2H), 4.08 (s, 3H), 4.92 (ABq, J=12 Hz, 2H), 5.39 (s, 1H)

EXAMPLE 17

Generally the same procedure as Example 16 gives the following compounds.

(1) Diphenylmethyl 3-acetoxymethyl-7-methoxyimino-3-cephem-4-carboxylate
mp 136°-144° C.
IR(nujol) 1790, 1730, 1715 $cm^{-1}$
NMR($CDCl_3$)δ 2.00 (s, 3H), 3.47 (ABq, J=18 Hz, 2H), 4.10 (s, 3H), 4.88 (ABq, J=14 Hz, 2H), 5.37 (s, 1H), 7.00 (s, 1H), 7.33 (s, 10H)

(2) Diphenylmethyl 7-methoxyimino-3-(1-methyl-1H-tetrazol-5-yl)thiomethyl-3-cephem-4-carboxylate
mp 209°-212° C. (dec)
IR(nujol) 1780, 1720, 1620 $cm^{-1}$
NMR(DMSO-$d_6$)δ 3.84 (m, 2H), 3.91 (s, 3H), 4.05 (s, 3H), 4.30 (ABq, J=13.5 Hz, 2H), 5.84 (s, 1H), 6.97 (s, 1H), 7.4 (m, 10H)

(3) 2,2,2-Trichloroethyl 7-(4-methoxybenzyloxyimino)-3-methyl-3-cephem-4-carboxylate
IR($CH_2Cl_2$) 1785, 1740, 1615 $cm^{-1}$
NMR($CDCl_3$)δ 2.20 (s, 3H), 3.35 (ABq, J=18 Hz, 2H), 3.82 (s, 3H), 4.92 (ABq, J=12 Hz, 2H), 5.22 (s, 2H), 5.37 (s, 1H), 7.12 (ABq, J=9 Hz, 4H)

EXAMPLE 18

In dimethylformamide (5 ml) are dissolved 2,2,2-trichloroethyl 3-methyl-7-oxo-3-cephem-4-carboxylate (691 mg) and hydroxylamine hydrochloride (139 mg), followed by addition of pyridine (162 μl) and methylene chloride (10 ml). The mixture is refluxed in a Dean-Stark trap packed with Molecular Sieve 3A for 45 minutes. The reaction mixture is concentrated under reduced pressure and the residue is dissolved in ethyl acetate. The resultant solution is washed with water and aqueous sodium chloride, dried over magnesium sulfate and concentrated under reduced pressure. The residual oil is subjected to silica gel (20 g) column chromatography and elution is carried out with 5–13% ethyl acetate-hexane to give 2,2,2-trichloroethyl 7-hydroxyimino-3-methyl-3-cephem-4-carboxylate as an oil (570 mg).

IR($CH_2Cl_2$) 3530, 1790, 1740 $cm^{-1}$

NMR($CDCl_3$)δ 2.09 (s, 3H), 3.28 (ABq, J=18 Hz, 2H), 4.81 (ABq, J=12 Hz, 2H), 5.31 (s, 1H), 9.39 (s, 1H)

EXAMPLE 19

Generally the same procedure as Example 18 gives the following compounds.

(1) Diphenylmethyl 3-acetoxymethyl-7-hydroxyimino-3-cephem-4-carboxylate
mp 112°-120° C.
IR($CHCl_3$) 1785, 1730 $cm^{-1}$ NMR(CDCl$_3$)δ 1.97 (s, 3H), 3.40 (ABq, J=18.5 Hz, 2H), 5.38 (s, 1H), 6.99 (s, 1H), 7.35 (m, 10H)

(2) Diphenylmethyl 7-hydroxyimino-3-(1-methyl-1H-tetrazol-5-yl)thiomethyl-3-cephem-4-carboxylate
mp 173°–4° C. (dec)
IR(nujol) 1775, 1715 cm$^{-1}$
NMR(DMSO-d$_6$)δ 3.90 (s, 3H), 4.28 (ABq, J=14 Hz, 2H), 5.78 (s, 1H), 6.97 (s, 1H), 7.40 (m, 10H), 13.13 (s, 1H)

EXAMPLE 20

In chloroform (70 ml) are dissolved 2,2,2-trichloroethyl 3-methyl-7-oxo-3-cephem-4-carboxylate (14.30 g), t-butyl carbazate (6.00 g) and pyridine hydrochloride (4.77 g) and the mixture is refluxed in a Dean-Stark trap packed with Molecular Sieve 3A for 30 minutes. The reaction mixture is washed with 1 N-HCl and water in that order, dried over magnesium sulfate and concentrated. The residual oil is subjected to silica gel (240 g) column chromatography and elution is carried out with ethyl acetate-benzene to give crystals of 2,2,2-trichloroethyl (E)-7-t-butoxycarbonylhydrazono-3-methyl-3-cephem-4-carboxylate (4.88 g).
mp 148°–9° C.
IR(nujol) 1780, 1750, 1740 cm$^{-1}$
NMR(DMSO-d$_6$)δ 1.50 (s, 9H), 2.17 (s, 3H), 3.67 (ABq, J=19 Hz, 2H), 5.10 (ABq, J=12 Hz, 2 H), 5.63 (s, 1H), 10.80 (s, 1H)
and crystals of 2,2,2-trichloroethyl (Z)-7-t-butoxycarbonylhydrazono-3-methyl-3-cephem-4-carboxylate (2.57 g).
mp 137°–140° C.
IR(nujol) 1790, 1740, 1710, 1665 cm$^{-1}$
NMR(DMSO-d$_6$)δ 1.53 (s, 9H), 2.33 (s, 3H), 3.45 (ABq, J=17 Hz, 2H), 5.07 (s, 2H), 5.57 (s, 1H), 11.37 (s, 1H)

EXAMPLE 21

Generally the same procedure as Example 20 gives the following compounds.
(1) Diphenylmethyl (E)-7-t-butoxycarbonylhydrazono-3-acetoxymethyl-3-cephem-4-carboxylate
mp 95°–100° C.
IR(nujol) 1740, 1720, 1702 cm$^{-1}$
NMR(DMSO-d$_6$)δ 1.47 (s, 9H), 1.97 (s, 3H), 3.67 (broad s, 2H), 4.78 (ABq, J=14 Hz, 2H), 5.63 (s, 1H), 6.93 (s, 1H), 7.1~7.7 (m, 10H), 11.00 (s, 1H)
and diphenylmethyl (Z)-7-t-butoxycarbonylhydrazono-3-acetoxymethyl-3-cephem-4-carboxylate
mp 99°–102° C.
IR(nujol) 1775, 1735, 1720 cm$^{-1}$
NMR(DMSO-d$_6$)δ 1.50 (s, 9H), 2.00 (s, 3H), 3.58 (broad s, 2H), 4.82 (ABq, J=13 Hz, 2H), 5.63 (s, 1H), 6.97 (s, 1H), 7.2~7.7 (m, 10H), 11.53 (s, 1H)
(2) Diphenylmethyl (E)-7-t-butoxycarbonylhydrazono-3-(1-methyl-1H-tetrazol-5-ylthiomethyl)-3-cephem-4-carboxylate
mp 148°~150° C. (dec)
IR(CH$_2$Cl$_2$) 1760, 1750, 1720 cm$^{-1}$
NMR(DMSO-d$_6$)δ 1.45 (s, 9H), 3.82 (s, 2H), 3.83 (s, 3H), 4.35 (ABq, J=13 Hz, 2H), 5.28 (s, 1H), 6.93 (s, 1H), 7.1~7.6 (m, 10H), 9.27 (s, 1H)
and diphenylmethyl (Z)-7-t-butoxycarbonylhydrazono-3-(1-methyl-1H-tetrazol-5-ylthiomethyl)-3-cephem-4-carboxylate
mp 146°–8° C. (dec)
IR(CH$_2$Cl$_2$) 1790, 1750, 1720 cm$^{-1}$
NMR (DMSO-d$_6$)δ 1.50 (s, 9H), 3.68 (broad s, 2H), 3.86 (s, 3H), 4.33 (ABq, J=14 Hz, 2H), 5.58 (s, 1H), 6.92 (s, 1H), 7.2~7.7 (m, 10H), 11.47 (s, 1H)

EXAMPLE 22

In tetrahydrofuran (25 ml) is dissolved 2,2,2-trichloroethyl 7-methoxyimino-3-methyl-3-cephem-4-carboxylate (5.80 g) and under ice-cooling stirring, a 1 M tetrahydrofuran solution of borane-tetrahydrofuran complex (198 ml) is added dropwise over a period of 80 minutes. The reaction mixture is diluted with water (20 ml), adjusted to pH 1 with dilute hydrochloric acid and stirred at room temperature for 1.5 hours. The organic solvent is distilled off, the residual aqueous solution is adjusted to pH 7 with aqueous sodium hydrogen carbonate and extracted with ethyl acetate. The ethyl acetate is then distilled off, the residue is dissolved in a mixture of methanol (120 ml) and 12.5% aqueous ammonium chloride (60 ml) and the mixture is stirred at room temperature for an hour. The organic solvent is distilled off and the residual aqueous solution is extracted with ethyl acetate. The extract is washed with aqueous sodium chloride, dried over magnesium sulfate and concentrated. The oily residue is subjected to silica gel (90 g) column chromatography and elution is carried out with ethyl acetate-methylene chloride. By the above procedure is obtained 2,2,2-trichloroethyl 7β-methoxyamino-3-methyl-3-cephem-4-carboxylate (3.51 g).
IR(CH$_2$Cl$_2$) 1780, 1740 cm$^{-1}$
NMR(CDCl$_3$)δ 2.20 (s, 3H), 3.38 (ABq, J=18 Hz, 2H), 3.58 (s, 3H), 4.91 (m, 4H), 6.20 (broad signal, 1H)

EXAMPLE 23

The following compounds are obtained by the same procedure as Example 22.
(1) Diphenylmethyl 3-acetoxymethyl-7β-methoxyamino-3-cephem-4-carboxylate.
mp 112°–115° C.
IR(nujol) 3250, 1790, 1735, 1710 cm$^{-1}$
NMR(DMSO-d$_6$)δ 1.97 (s, 3H), 3.44 (s, 3H), 3.55 (ABq, J=20 Hz, 2H), 4.70 (ABq, J=12 Hz, 2H), 508 (s, 2H), 6.85 (s, 1H), 7.36 (m, 10H)

EXAMPLE 24

In dry tetrahydrofuran (200 ml) is suspended sodium borohydride (3.80 g) and under ice-cooling, boron trifluoride etherate (25.3 ml) is added dropwise over a period of 40 minutes. The mixture is stirred at the same temperature for a further 10 minutes, after which it is filtered in a nitrogen gas stream. After the filtrate is cooled with ice, methanol (5.20 g) is added. The mixture is stirred until gases cease to evolve. Then, 50 ml of this mixture is added to a solution of diphenylmethyl 7-methoxyimino-3-(1-methyl-1H-tetrazol-5-ylthiomethyl)-3-cephem-4-carboxylate (2.05 g) in tetrahydrofuran (200 ml) under ice-cooling, and the resultant mixture is stirred at that temperature. After 25 minutes, a further 15 ml portion of the above mixture is added and the stirring is further continued for 15 minutes. At the end of this reaction, water (60 ml) is added dropwise and the mixture is adjusted to pH 1 with 1 N-HCl and stirred at room temperature for an hour. The organic solvent is then distilled off and the residual aqueous solution is adjusted to pH 7 with aqueous sodium hydrogen carbonate and extracted with ethyl acetate. The extract is concentrated, the residue is dissolved in a mixture of tetrahydrofuran (40 ml) and 12.5% aqueous ammonium chloride (30 ml), and the mixture is stirred for an hour, followed by addition of ethyl acetate. The mixture is washed with water and aqueous sodium chloride in that order, dried over magnesium sulfate and concentrated under reduced pressure. The residual oil is subjected to silica gel (45 g) column chromatography and elution is carried out with ethyl acetate and methylene chloride. By the above procedure are obtained crystals of diphenylmethyl 7 β-methoxyamino-3-(1-methyl-1H-tetrazol-5-ylthiomethyl)-3-cephem-4-carboxylate (1.05 g).

MP 128°–137° C. (dec)

IR(CH$_2$Cl$_2$) 1780, 1730 cm$^{-1}$

NMR(CDCl$_3$)δ 3.58 (s, 3H), 3.72 (s, 2H), 3.82 (s, 3H), 4.34 (ABq, J=14 Hz, 2H), 4.96 (broad signal, 2H), 6.1 (broad signal, 1H), 6.93 (s, 1H), 7.35 (s, 10H)

EXAMPLE 25

In ethanol (0.6 ml) is dissolved 2,2,2-trichloroethyl 7-hydroxyimino-3-methyl-3-cephem-4-carboxylate (100 mg) and under ice-cooling, a solution of borane-pyridine complex (102 mg) in ethanol (0.7 ml) is added. Then, a 2 N-methanolic solution of hydrogen chloride (0.6 ml) is added dropwise in a nitrogen stream and the mixture is stirred at the same temperature for 3 hours. The mixture is further stirred at room temperature for an hour, after which time it is diluted with ethyl acetate, washed with water and aqueous sodium chloride in that order, dried over magnesium sulfate and concentrated under reduced pressure. The oily residue is subjected to silica gel (4.5 g) column chromatography and elution is carried out with ethyl acetate-hexane to give 2,2,2-trichloroethyl 7 β-hydroxyamino-3-methyl-3-cephem-4-carboxylate (79 mg) as an amorphous solid.

IR(CH$_2$Cl$_2$) 3550, 1780, 1740 cm$^{-1}$

NMR(CDCl$_3$)δ 2.25 (s, 3H), 3.40 (s, 2H), 4.93 (m, 4H), 5.77 (br s, 2H)

EXAMPLE 26

Generally the same procedure as Example 25 gives the following compounds.

(1) Diphenylmethyl 3-acetoxymethyl-7β-hydroxyamino-3-cephem-4-carboxylate m.p. 167°–168° C. (decomp.)

IR(nujol) 3380, 1760, 1732, 1722 cm$^{-1}$

NMR(DMSO-d$_6$)δ 1.96 (s, 3H), 3.53 (ABq, J=16.5 Hz, 2H), 4.69 (ABq, J=13 Hz, 2H), 5.03 (m, 2H), 6.43 (dd, J=3.7 Hz, 1H), 6.90 (s, 1H), 7.34 (m, 10H), 7.70 (d, J=3 Hz, 1H)

(2) Diphenylmethyl 7β-hydroxyamino-3-(1-methyl-1H-tetrazol-5-ylthiomethyl)-3-cephem-4-carboxylate mp 168°–9° C. (dec)

IR(nujol) 3320, 1780, 1730 cm$^{-1}$

NMR(DMSO-d$_6$+D$_2$O)δ 3.67 (br s, 2H), 3.87 (s, 3H), 4.22 (ABq, J=13 Hz, 2H), 4.97 (d, J=5 Hz, 1H), 5.06 (d, J=5 Hz, 1H), 6.90 (s, 1H)

EXAMPLE 27

In tetrahydrofuran (20 ml) is dissolved 2,2,2-trichloroethyl (E)-7-t-butoxycarbonylhydrazono-3-methyl-3-cephem-4-carboxylate (4.60 g), and under ice-cooling, a 1 M tetrahydrofuran solution of borane-tetrahydrofuran complex (23 ml) is added dropwise. The mixture is stirred at that temperature for 30 minutes. The reaction mixture is poured in a mixture of ethyl acetate (150 ml) and aqueous sodium chloride (200 ml). The organic layer is taken, dried over magnesium sulfate and concentrated. The residual oil is subjected to silica gel (50 g) column chromatography and elution is carried out with ethyl acetate-benzene. The above procedure gives crystals of 2,2,2-trichloroethyl 7β-t-butoxycarbonylhydrazino-3-methyl-3-cephem-4-carboxylate (2.49 g).

mp 142°–3° C.

IR(nujol) 1790, 1720 cm$^{-1}$

NMR(CDCl$_3$)δ 1.50 (s, 9H), 2.23 (s, 3H), 3.33 (broad s, 2H), 4.60 (broad signal, 1H), 4.87 (ABq, J=9 Hz, 2H), 4.80 (d, J=4.5 Hz, 1H), 4.92 (d, J=4.5 Hz, 1H), 6.20 (broad signal, 1H)

EXAMPLE 28

Generally the same procedure as Example 27 gives the following compounds.

(1) Diphenylmethyl 3-acetoxymethyl-7β-t-butoxycarbonylhydrazino-3-cephem-4-carboxylate mp 146°–8° C.

IR(nujol) 1785, 1725, 1710, 1695 cm$^{-1}$

NMR(CDCl$_3$)δ 1.50 (s, 9H), 2.00 (s, 3H), 3.42 (ABq, J=17 Hz, 2H), 4.58 (d, J=4 Hz, 1H), 4.7∼5.1 (m, 4H), 6.34 (d, J=4 Hz, 1H), 6.92 (s, 1H), 7.1∼7.6 (m, 10H)

(2) Diphenylmethyl 7β-t-butoxycarbonylhydrazino-3-(1-methyl-1H-tetrazol-5-ylthiomethyl-3-cephem-4-carboxylate IR(CH$_2$Cl$_2$) 1790, 1720 cm$^{-1}$ NMR(CDCl$_3$)δ 1.50 (s, 9H), 3.73 (broad s, 2H), 3.87 (s, 3H), 4.38 (ABq, J=14 Hz, 2H), 4.62 (d, J=4 Hz, 1H), 4.93 (d, J=5 Hz, 1H), 4.97 (d, J=5 Hz, 1H), 6.25 (d, J=4 Hz, 1H), 7.98 (s, 1H), 7.2∼7.7 (m, 10H)

EXAMPLE 29

In methylene chloride (10 ml) are dissolved 2,2,2-trichloroethyl 7β-methoxyamino-3-methyl-3-cephem-4-carboxylate (320 mg) and pyridine (134 mg) and the mixture is cooled to −25° C. To this mixture is added phenoxyacetyl chloride (171 mg), followed by stirring for 20 minutes. The reaction mixture is poured in a mixture of ethyl acetate and water and the organic layer is taken. The organic layer is washed with 1 N-HCl, aqueous sodium hydrogen carbonate and aqueous sodium chloride in that-order, dried over magnesium sulfate and concentrated. The above procedure gives 2,2,2-trichloroethyl 7-(N-methoxy-2-phenoxyacetamido)-3-methyl-3-cephem-4-carboxylate (510 mg).

IR(CH$_2$Cl$_2$) 1785, 1740, 1700 cm$^{-1}$

NMR(CDCl$_3$)δ 2.40 (s, 3H), 3.33 (ABq, J=16 Hz, 2H), 4.02 (s, 3H), 4.93 (s, 2H), 5.03 (ABq, J=unidentified, 2H), 5.11 (d, J=4 Hz, 1H), 5.56 (d, J=4 Hz, 1H), 6.9∼7.5 (m, 5H)

EXAMPLE 30

Generally the same procedure as Example 29 gives the following compounds.

(1) 2,2,2-Trichloroethyl 7-[N-methoxy-2-D-(2,2,2-trichloroethoxycarbonylamino)-2-phenylacetamido]-3-methyl-3-cephem-4-carboxylate IR(CH$_2$Cl$_2$) 3420, 1790, 1740, 1680 cm$^{-1}$ NMR(CDCl$_3$)δ 2.25 (s, 3H), 3.14 (ABq, J=18 Hz, 2H), 3.95 (s, 3H), 4.74 (s, 2H), 4.90 (s, 2H), 4.98 (d, J=4 Hz, 1H), 5.75 (d, J=8 Hz, 1H), 5.80 (d, J=4 Hz, 1H), 6.33 (d, J=8 Hz, 1H), 7.43 (s, 5H)

(2) Diphenylmethyl 3-acetoxymethyl-7-[N-methoxy-2-(2-thienyl)acetamido]-3-cephem-4-carboxylate IR(CH$_2$Cl$_2$) 1790, 1740, 1680 cm$^{-1}$ NMR(CDCl$_3$)δ 2.04 (s, 3H), 3.38 (s, 2H), 3.96 (s, 3H), 4.13 (s, 2H), 5.01 (ABq, J=14 Hz, 2H), 5.00 (d, J=4 Hz, 1H), 5.90 (d, J=4 Hz, 1H), 7.0∼7.3 (m, 13H)

(3) Diphenylmethyl 3-acetoxymethyl-7-(N-methoxy-2-cyanomethylthioacetamido)-3-cephem-4-carboxylate.
mp 162°-5° C.
IR(nujol) 1780, 1740, 1730, 1660 cm$^{-1}$
NMR(acetone-d$_6$)δ 1.98 (s, 3H), 3.54 (s, 2H), 3.72 (s, 2H), 3.83 (s, 2H), 3.91 (s, 3H), 4.99 (ABq, J=14 Hz, 2H), 5.20 (d, J=4 Hz, 1H), 6.00 (d, J=4 Hz, 1H), 6.96 (s, 1H), 7.3~7.4 (m, 10H)

(4) Diphenylmethyl 3-acetoxymethyl-7-[N-methoxy-2-(2-formylamino-1,3-thiazol-4-yl)acetamido]-3-cephem-4-carboxylate
IR(CH$_2$Cl$_2$) 1785, 1730, 1700, 1680 cm$^{-1}$
NMR(CDCl$_3$)δ 2.02 (s, 3H), 3.37 (s, 2H), 3.92 (s, 3H), 4.02 (s, 2H), 4.98 (d, J=4 Hz, 1H), 5.00 (ABq, J=14 Hz, 2H), 5.92 (d, J=4 Hz, 1H), 6.90 (s, 1H), 6.98 (s, 1H), 7.39 (s, 10H), 8.70 (s, 1H), 11.10 (broad s, 1H)

(5) Diphenylmethyl 3-acetoxymethyl-7-(N-methoxy-2-formyloxy-2-phenylacetamido)-3-cephem-4-carboxylate
NMR(CDCl$_3$)δ 2.00 (s, 3H), 3.20 (s, 2H), 4.06 (s, 3H), 4.90 (ABq, J=14 Hz, 2H and d, J=4 Hz, 1H), 5.93 (d, J=4 Hz, 1H), 6.40 (s, 1H), 6.96 (s, 1H), 7.2~7.6 (m, 15H), 8.22 (s, 1H)

(6) Diphenylmethyl 3-acetoxymethyl-7-(N-methoxy-2-diphenylmethoxycarbonyl-2-phenylacetamido)-3-cephem-4-carboxylate
IR(CH$_2$Cl$_2$) 1790, 1740, 1680 cm$^{-1}$
NMR(CDCl$_3$)δ 2.00 (s, 3H), 3.26 (ABq, J=unidentified, 2H), 3.54 and 3.76 (two s, 3H), 4.9~5.3 (m, 3H), 5.18 and 5.21 (two s, 1H), 5.40 and 5.43 (two s, 1H), 5.93 and 5.97 (two d, J=5 Hz, 1H), 6.9~7.4 (m, 27H)

(7) Diphenylmethyl 7-[N-methoxy-2-(2-thienyl)acetamido]-3-(1-methyl-1H-tetrazol-5-ylthiomethyl)-3-cephem-4-carboxylate
IR(CH$_2$Cl$_2$) 1785, 1720, 1680 cm$^{-1}$
NMR(CDCl$_3$)δ 3.61 (s, 2H), 3.85 (s, 3H), 3.94 (s, 3H), 4.12 (s, 2H), 4.45 (ABq, J=14 Hz, 2H), 5.00 (d, J=4 Hz, 1H), 5.89 (d, J=4 Hz, 1H), 6.8~7.6 (m, 12H)

(8) 2,2,2-Trichloroethyl 7-(N-hydroxy-2-phenoxyacetamido)-3-methyl-3-cephem-4-carboxylate
mp 196°-7° C. (dec)
IR(CHCl$_3$) 3700, 1790, 1740, 1700 cm$^{-1}$
NMR(CDCl$_3$-DMSO-d$_6$)δ 2.33 (s, 3H). 3.41 (ABq, J=unidentified, 2H), 4.90 (s, 2H), 5.00 (s, 2H), 5.11 (d, J=4 Hz, 1H), 5.95 (d, J=4 Hz, 1H), 7.10 (m, 5H), 10.36 (s, 1H)

(9) Diphenylmethyl 3-acetoxymethyl-7-[N-hydroxy-2-(2-thienyl)acetamido]-3-cephem-4-carboxylate
mp 196°-7° C. (dcc)
IR(CHCl$_3$) 1785, 1730, 1675 cm$^{-1}$
NMR(CDCl$_3$)δ 2.03 (s, 3H), 3.43 (br s, 2H), 4.07 (s, 2H), 4.97 (ABq, J=14 Hz, 2H), 4.97 (d, J=5 Hz, 1H), 6.03 (d, J=5 Hz, 1H), 6.97 (s, 1H), 6.9~7.5 (m, 13H), 7.80 (s, 1H)

(10) Diphenylmethyl 7-[N-hydroxy-2-(2-thienyl)acetamido]-3-(1-methyl-1H-tetrazol-5-ylthiomethyl)-3-cephem-4-carboxylate
IR(CHCl$_3$) 1785, 1720, 1675 cm$^{-1}$
NMR(CDCl$_3$)δ 3.60 (ABq, J=18 Hz, 2H), 3.78 (s, 3H), 4.05 (s, 2H), 4.31 (ABq, J=14 Hz, 2H), 4.92 (d, J=5 Hz, 1H), 6.02 (d, J=4 Hz, 1H), 6.91 (s, 1H), 6.8~7.5 (m, 13H)

(11) Diphenylmethyl 7-[N-hydroxy-2-(1H-tetrazol-1-yl)-acetamido]-3-(1-methyl-1H-tetrazol-5-ylthiomethyl)-3-cephem-4-carboxylate
IR(CHCl$_3$) 1780, 1680~1720 (broad) cm$^{-1}$
NMR(CDCl$_3$)δ 3.62 (br s, 2H), 3.78 (s, 3H), 4.33 (br s, 2H), 4.98 (d, J=5 Hz, 1H), 5.65 (br s, 2H), 5.98 (d, J=5 Hz, 1H), 6.93 (s, 1H), 7.1~7.5 (m, 10H), 8.90 (s, 1H), 9.73 (br s, 1H)

(12) 2,2,2-Trichloroethyl 7-(N-t-butoxycarbonylamino-2-phenoxyacetamido)-3-methyl-3-cephem-4-carboxylate
mp 182°-3° C.
IR(nujol) 1760, 1750, 1740, 1720 cm$^{-1}$
NMR(CDCl$_3$)δ 1.50 (s, 9H), 2.20 (s, 3H), 3.42 (ABq, J=18 Hz, 2H), 4.85 (s, 2H), 4.90 (ABq, J=14 Hz, 2H), 5.01 (d, J=5 Hz, 1H), 5.98 (d, J=5 Hz, 1H), 6.8~7.1 (m, 2H), 7.26 (s, 5H)

(13) Diphenylmethyl 3-acetoxymethyl-7-[N-t-butoxycarbonylamino-2-(2-thienyl)acetamido]-3-cephem-4-carboxylate
IR(CH$_2$Cl$_2$) 1790, 1735, 1690 cm$^{-1}$
NMR(CDCl$_3$)δ 1.97 (s, 9H), 3.40 (br s, 2H), 3.95 (ABq, J=10 Hz, 2H), 4.87 (ABq, J=13 Hz, 2H), 4.92 (d, J=5 Hz, 1H), 5.97 (d, J=5 Hz, 1H), 6.73 (s, 1H), 6.8~7.1 (m, 3H), 7.1~7.6 (m, 11H)

(14) Diphenylmethyl 7-[N-t-butoxycarbonylamino-2-(2-thienyl)acetamido]-3-(1-methyl-1H-tetrazol-5-ylthiomethyl)-3-cephem-4-carboxylate
IR(CH$_2$Cl$_2$) 1790, 1740, 1690 cm$^{-1}$
NMR(CDCl$_3$)δ 1.53 (s, 9H), 3.70 (br s, 2H), 3.80(s, 3H), 3.97(ABq, J=10 Hz), 4.33(ABq, J=14 Hz, 2H), 4.95(d, J=5 Hz, 1H), 5.98(d, J=5 Hz, 1H), 6.63(s, 1H), 6.8~7.1(m, 3H), 7.1~7.6(m, 11H)

(15) Diphenylmethyl 7-[N-t-butoxycarbonylamino-(2-D-formyloxy-2-phenylacetamido)-3-(1-methyl-1H-tetrazol-5-ylthiomethyl)-3-cephem-4-carboxylate
IR(CH$_2$Cl$_2$) 1790, 1740~1700(broad)cm$^{-1}$
NMR(CDCl$_3$)δ 1.50(s, 9H), 3.62(s, 2H), 3.80(s, 3H), 4.24(s, 2H), 4.92(d, J=5 Hz, 1H), 6.00(d, J=5 Hz, 1H), 6.36(s, 1H), 6.88(s, 1H), 7.1~7.6(m, 15H), 8.12(s, 1H)

EXAMPLE 31

2,2,2-Trichloroethyl 7-(N-methoxy-2-phenoxyacetamido)-3-methyl-3-cephem-4-carboxylate (490 mg) is dissolved in a mixture of methylene chloride (15 ml), acetic acid (4 ml) and dimethylformamide (4 ml), and under ice-cooling, zinc dust (400 mg) is added. The mixture is stirred at room temperature for 1.5 hours, at the end of which time acetic acid (10 ml), dimethylformamide (2 ml) and zinc dust (300 mg) are further added and stirred for another 1.5 hours. The reaction mixture is diluted with ethyl acetate and filtered. The filtrate is washed with 0.5 N-HCl and aqueous sodium chloride in that order, dried over magnesium sulfate and concentrated. The resultant crude crystals are washed with ether-ethyl acetate to give 7-(N-methoxy-2-phenoxyacetamido)-3-methyl-3-cephem-4-carboxylic acid (141 mg).
mp 185°-8° C. (dec)
IR(nujol) 3220, 1765, 1730, 1700 cm$^{-1}$
NMR(acetone -d$_6$)δ 2.24(s, 3H), 3.34(ABq, J=18 Hz, 2H), 3.96(s, 3H), 5.06(s, 2H), 5.11(d, J=4Hz, 1H), 5.80(d, J=4 Hz, 1H), 6.8~7.4(m, 5H)

EXAMPLE 32

Generally the same procedure as Example 31 gives the following compounds.

(1) 7-Methoxyimino-3-methyl-3-cephem-carboxylic acid
mp 150°-151° C. (dec)
IR(nujol) 1775, 1700, 1670(sh)cm$^{-1}$
NMR(acetone-d$_6$)δ 3.55(ABq, J=18 Hz, 2H), 4.03(s, 3H), 5.56(s, 1H), 8.3(broad signal, 1H)

(2) 7-(N-hydroxy-2-phenoxyacetamido)-3-methyl-3-cephem-4-carbocarboxylic acid mp 115°–125° C.
IR(nujol) 1760, 1660–1690(broad)cm$^{-1}$
NMR(CDCl$_3$)δ 2.20(s, 3H), 3.27(ABq, J=14 Hz, 2H), 5.03(m, 3H), 5.95(d, J=4 Hz, 1H), 6.77~7.43(m, 5H), 8.77(br s, 2H)

(3) 7-(N-t-butoxycarbonylamino-2-phenoxyacetamido)-3-methyl-cephem-carboxylic acid
IR(CH$_2$Cl$_2$) 1790, 1740, 1720 cm$^{-1}$
NMR(CDCl$_3$)δ 1.50(s, 9H), 2.53(s, 3H), 3.38(br s, 2H), 4.88(s, 2H), 5.00(d, J=5 Hz, 1H), 5.87(d, J=5 Hz, 1H)

EXAMPLE 33

In formic acid (25 ml) is dissolved 2,2,2-trichloroethyl 7-[N-methoxy-D-2-phenyl-2-(2,2,2-trichloroethoxycarbonylamino)acetamido]-3-methyl-3-cephem-4-carboxylate (500 mg), and under ice-cooling, zinc dust (700 mg) is added. The mixture is stirred at room temperature for 30 minutes.

After addition of zinc dust (200 mg), the mixture was stirred for 30 minutes. The reaction mixture is filtered and the filtrate is concentrated under reduced pressure. To the residue is added benzene, followed by concentration under reduced pressure. This procedure is repeated further twice, and after addition of water, the insolubles are filtered off. Hydrogen sulfide gas is bubbled through the filtrate and the resultant precipitate is filtered off. The filtrate is adjusted to pH 7 with aqueous sodium hydrogen carbonate, filtered again, readjusted to pH 1 with 1 N-HCl and subjected to column chromatography on nonionic adsorbent resin HP-20® (Mitsubishi Kasei K.K.), elution being carried out with 10% isopropyl alcohol. The eluate is lyophilized to give a powder of 7-(D-2-amino-N-methoxy-2-phenylacetamido)-3-methyl-3-cephem-4-carboxylic acid hydrochloride (105 mg).

IR(nujol) ~3400(broad), 1765, 1680 cm$^{-1}$
NMR(D$_2$O)δ 1.98(s, 3H), 3.26(ABq, J=18 Hz, 2H), 3.74(s, 3H), 5.08(d, J=4 Hz, 1H), 5.56(s, 1H), 5.76(d, J=4 Hz, 1H), 7.54(s, 5H)

EXAMPLE 34

Generally the same procedure as Example 33 gives sodium 3-acetoxymethyl-7-(N-methoxy-2-cyanomethylthioacetamido)-3-cephem-4-carboxylate
IR(nujol) 2220, 1780, 1665, 1600 cm$^{-1}$
NMR(D$_2$O)δ 2.13(s, 3H), 3.57(ABq, J=18 Hz, 2H), 3.70(s, 2H), 3.90(s, 2H), 3.96(s, 3H), 4.88(ABq, J=14 Hz, 2H), 5.24(d, J=4.5 Hz, 1H), 5.89(d, J=4.5 Hz, 1H)

EXAMPLE 35

In methylene chloride (5 ml) is dissolved diphenylmethyl 3-acetoxymethyl-7-[N-methoxy-2-(2-thienyl)acetamido]-3-cephem-4-carboxylate (273 mg), and under ice-cooling, anisole (0.5 ml) and trifluoroacetic acid (1.0 ml) are added. The mixture is stirred for 100 minutes. The reaction mixture is concentrated under reduced pressure and the residue is dissolved in ethyl acetate and extracted with a dilute aqueous solution of sodium hydrogen carbonate. The water layer is adjusted to pH 1 with 3 N-HCl and extracted with ethyl acetate. The extract is washed with aqueous sodium chloride, dried over magnesium sulfate and concentrated under reduced pressure to give an oil (190 mg). This oily residue is dissolved in acetone (1 ml), followed by addition of a solution of sodium 2-ethylhexanoate in acetone (1 ml, 0.4 mmol). This solution is concentrated under reduced pressure, and ether is added to the residue, whereby sodium 3-acetoxymethyl-7-[N-methoxy-2-(2-thienyl)acetamido]3-cephem-4-carboxylate (140 mg) is obtained.

mp 104°–112° C. (dec)
IR(nujol) 1760, 1680, 1610 cm$^{-1}$
NMR(D$_2$O)δ 2.14(s, 3H), 3.48(ABq, J=19 Hz, 2H), 3.94(s, 3H), 4.20(s, 2H), 4.96(ABq, J=unidentified, 2H), 5.13(d, J=4Hz, 1H), 5.89(d, J=4 Hz, 1H), 7.1~7.5(m, 3H)

EXAMPLE 36

In methylene chloride (10 ml) is dissolved diphenylmethyl 3-acetoxymethyl-7-[N-methoxy-2-(2-formylamino-1,3-thiazol-4-yl)acetamido]-3-cephem-4-carboxylate (535 mg). Under ice-cooling, anisole (1 ml) and trifluoroacetic acid (1.5 ml) are added and the mixture is stirred for 1.5 hours. The reaction mixture is concentrated under reduced pressure and the residue is dissolved in ethyl acetate and extracted with a dilute aqueous solution of sodium hydrogen carbonate. The water layer is adjusted to pH 1 with dil HCl and extracted with ethyl acetate. The extract is washed with aqueous sodium chloride, dried over magnesium sulfate, and concentrated under reduced pressure. The residue is washed with isopropyl ether to give a powder of 3-acetoxymethyl-7-[N-methoxy-2-(2-formylamino-1,3-thiazol-4-yl)acetamido]-3-cephem-4-carboxylic acid (390 mg).

IR(CH$_2$Cl$_2$) 1780, 1740, 1700, 1680(sh)cm$^{-1}$
NMR(acetone-d$_6$)δ 2.00(s, 3H), 3.46(ABq, J=unidentified, 2H), 3.85(s, 3H), 4.02(s, 2H), 5.01(ABq, J=15 Hz, 2H), 5.07(d, J=4 Hz, 1H), 6.00(d, J=4 Hz, 1H), 7.12(s, 1H), 8.66(s, 1H)

EXAMPLE 37

Generally the same procedure as Example 36 gives the following compounds.

(1) 3-Acetoxymethyl-7-(N-methoxy-2-formyloxy-2-phenylacetamido)-3-cephem-4-carboxylic acid
IR(nujol) 1785, 1730, 1690(sh), 1640(sh)cm$^{-1}$
NMR(acetone-d$_6$)δ 2.00(s, 3H), 3.36(ABq, J=20 Hz), 4.00(s, 3H), 4.96(ABq, J=14 Hz, 2H), 5.04(d, J=5 Hz, 1H), 5.98(d, J=5 Hz, 1H), 6.42(s, 1H), 7.3~7.8(m, 5H), 8.24(s, 1H)

(2) 3-Acetoxymethyl-7-(N-methoxy-2-carboxy-2-phenylacetamido)-3-cephem-4-carboxylic acid
IR(nujol) 1780, 1730, 1680(sh)cm$^{-1}$
NMR(acetone-d$_6$)δ 2.06(s, 3H), 3.50(m, 2H), 3.82 and 3.98(two s, 3H), 5.03(ABq, J=15 Hz, 2H), 5.15 and 5.21(two s, 1H), 5.27(d, J=4 Hz, 1H), 6.01 and 6.06(two d, J=4 Hz, 1H), 7.4(m, 5H), 8.13(broad signal, 2H)

(3) 7[N-methoxy-2-(2-thienyl)acetamido]-3-(1-methyl-1H-tetrazol-5-ylthiomethyl)-3-cephem-4-carboxylic acid
IR(nujol) 1780, 1720, 1680 cm$^{-1}$
NMR(DMSO-d$_6$)δ 3.60(br s, 2H), 3.80(s, 3H), 3.92(s, 3H), 4.10(ABq, J=13 Hz, 2H), 5.06(d, J=4 Hz, 1H), 5.97(d, J=4 Hz, 1H), 6.9(m, 2H), 7.4(m, 1H)

(4) 3-Acetoxymethyl-7-[N-hydroxy-2-(2-thienyl)acetamido]-3-cephem-4-carboxylic acid
mp 138°–140° C. (dec)
IR(KBr) 1775 cm$^{-1}$
NMR(DMSO-d$_6$)δ 2.01(s, 3H), 3.38(ABq, J=17 Hz, 2H), 4.08(s, 2H), 4.92(ABq, J=12 Hz, 2H), 5.02(d, J=5 Hz, 1H), 5.97(d, J=5 Hz, 1H), 6.9–7.5(m, 3H)

(5) 7-[N-hydroxy-2-(2-thienyl)acetamido]-3-(1-methyl-1H-tetrazol-5-ylthiomethyl)-3-cephem-4-carboxylic acid
mp 110°–155° C. (dec)
IR(nujol) 1775 cm$^{-1}$ NMR(DMSO-d$_6$)δ 3.60(s, 2H), 3.90(s, 3H), 4.00(s, 2H), 4.30(ABq, J=13 Hz, 2H), 5.07(d, J=5 Hz, 1H), 6.10(d, J=5 Hz, 1H), 6.9~7.4(m, 3H)

(6) 7-[N-hydroxy-2-(1H-tetrazol-1-yl)acetamido]-3-(1-methyl-1H-tetrazol-5-ylthiomethyl)-3-cephem-4-carboxylic acid mp 154°–180° C. (dec)

IR(nujol) 1770, 1685 cm$^{-1}$

NMR(DMSO-d$_6$)δ 3.66(s, 2H), 3.95(s, 3H), 4.35(ABq, J=1.35 Hz, 2H), 5.13(d, J=5 Hz, 1H), 5.66(s, 2H), 6.11(d, J=5 Hz, 1H), 9.43(s, 1H)

(7) 3-Acetoxymethyl-7-[1-{2-(2-thienyl)acetyl}hydrazino]-3-cephem-4-carboxylic acid IR(nujol) 1760~1740(broad)cm$^{-1}$ NMR(CD$_3$OD)δ 2.06(s, 3H), 3.35(ABq, J=18 Hz, 2H), 4.16(s, 2H), 4.88(br s, 2H), 5.10(d, J=5 Hz, 1H), 5.98(d, J=5 Hz, 1H), 6.8~7.1(m, 2H), 7.1~7.4(m, 1H)

(8) 3-(1-Methyl-1H-tetrazol-5-ylthiomethyl)-7-[1-{2-(2-thienyl)acetyl}hydrazino]-3-cephem-4-carboxylic acid mp 133°–140° C. (dec)

IR(nujol) 1770~1730(broad)cm$^{-1}$

NMR(DMSO-d$_6$)δ 3.50(br s, 2H), 3.90(s, 3H), 4.95(d, J=5 Hz, 1H), 5.85(d, J=5 Hz, 1H), 6.9~7.1(m, 2H), 7.32(m, 1H)

(9) 3-(1-Methyl-1H-tetrazol-5-ylthiomethyl)-7-[1-(2-formyloxy-2-phenylacetyl)hydrazino]-3-cephem-4-carboxylic acid IR(nujol) 1775, 1760, 1680 cm$^{-1}$ NMR(D$_2$O)δ 3.55(br s, 2H), 4.00(s, 3H), 4.15(br s, 2H), 5.10(d, J=5 Hz, 1H), 5.37(s, 1H), 6.90(d, J=5 Hz, 1H), 8.10(s, 1H)

(10) 3-Acetoxymethyl-7-methoxyimino-3-cephem-4-carboxylic acid mp 131.5°–133° C. (dec)

IR(nujol) 3100(sh), 1795, 1735, 1720, 1680, 1610 cm$^{-1}$

NMR(acetone-d$_6$)δ 2.03(s, 3H), 3.67(ABq, J=18 Hz, 2H), 4.04(s, 3H), 4.96(ABq, J=14 Hz, 2H), 5.67(s, 1H), 8.80(broad signal, 1H)

(11) 3-Acetoxymethyl-7-methoxyimino-3-cephem-4-carboxylic acid 1,1-dioxide mp 134°–140° C. (dec)

IR(nujol) 1800, 1735, 1675, 1620 cm$^{-1}$

NMR(acetone-d$_6$)δ 2.06(s, 3H), 4.12(s, 3H), 4.25(ABq, J=20 Hz, 2H), 4.97(ABq, J=14 Hz, 2H), 5.97(s, 1H), 8.30(broad signal, 1H)

EXAMPLE 38

Anisole (0.2 ml) is added to trifluoroacetic acid (4.1 ml), and under ice-cooling, 7-[N-t-butoxycarbonylamino-2-phenoxyacetamido]-3-methyl-3-cephem-4-carboxylic acid (820 mg) is added. The mixture is stirred at that temperature for 2 hours. The reaction mixture is concentrated under reduced pressure and the residue is treated with isopropyl ether to give a powder. The powder is washed with ethyl acetate to obtain 7-[1-(2-phenoxyacetyl)hydrazino]-3-methyl-3-cephem-4-carboxylic acid (324 mg).

IR(CH$_2$Cl$_2$) 1760, 1705, 1680, 1600 cm$^{-1}$

NMR(DMSO-d$_6$)δ 2.10(s, 3H), 3.45(s, 2H), 3.0~3.8(s, 2H), 5.05(d, J=4.5 Hz, 1H), 5.10(s, 2H), 5.70 (d, J=4.5 Hz, 1H), 7.5~6.8(m, 5H)

EXAMPLE 39

In methanol (10 ml) is dissolved 3-acetoxymethyl-7-[N-methoxy-2-(2-formylamino-1,3-thiazol-4-yl)acetamido]-3-cephem-4-carboxylic acid (462 mg) and under ice-cooling, concentrated HCl (0.1 ml) is added. After the mixture is stirred for 40 minutes, conc. hydrochloric acid (0.1 ml) is added.

The mixture is stirred at that temperature for an hour, at the end of which time it is concentrated under reduced pressure. The residue is dissolved in water (5 ml) and adjusted to pH 4 with aqueous sodium hydrogen carbonate. The insolubles are filtered off and the filtrate is subjected to column chromatography on nonionic resin HP-20 ® (Mitsubishi Kasei), elution being carried out with water-methanol (4:1 to 5:2). The eluate is lyophilized to give 3-acetoxymethyl-7-[N-methoxy-2-(2-amino-1,3-thiazol-4-yl)acetamido]-3-cephem-4-carboxylic acid (100 mg).

IR(nujol) 1770, 1730(sh), 1670(sh), 1630 cm$^{-1}$

NMR(D$_2$O)δ 2.12(s, 3H), 3.52(ABq, J=18 Hz, 2H), 3.92(s, 3H+2H), 4.86(ABq, J=unidentified, 2H), 5.17(d, J=4 Hz, 1H), 5.87(d, J=4 Hz, 1H), 6.62(s, 1H)

EXAMPLE 40

In ether (6 ml) is dissolved diphenylmethyl 3-acetoxymethyl-7-hydroxyimino-3-cephem-4-carboxylate (349 mg), and under ice-cooling, an ethereal solution of diazomethane (1 ml, 0.77 mmol) is added. While the temperature raised gradually to room temperature, the mixture is stirred for an hour. The reaction mixture is then concentrated under reduced pressure and the residue is purified by thin-layer chromatography (developer: ethyl acetate-hexane=1:1) to give diphenylmethyl 3-acetoxymethyl-7-methoxyimino-3-cephem-4-carboxylate (75 mg).

mp 150°–151° C.

IR(nujol) 1790, 1730, 1715 cm$^{-1}$

NMR(CDCl$_3$)δ 2.00(s, 3H), 3.47(ABq, J=18 Hz, 2H), 4.10(s, 3H), 4.88(ABq, J=14 Hz, 2H), 5.37(s, 1H), 7.00(s, 1H), 7.33(s, 10H)

and diphenylmethyl 3-acetoxymethyl-7-methylimino-3-cephem-4-carboxylate N-oxide (125 mg).

I.R.(CHCl$_3$) 1778, 1735 cm$^{-1}$

N.M.R.(CDCl$_3$) 2.00(s,3H), 3.46(ABq, J=18 Hz, 2H), 3.80(s,3H), 4.88(ABq, J=14 Hz, 2H), 5.53(s,1H), 7.06(s,1H), 7.3–7.6(m, 10H)

EXAMPLE 41

In methylene chloride (30 ml) is dissolved diphenylmethyl 3-acetoxymethyl-7-methoxyimino-3-cephem-4-carboxylate (1.00 g), and under ice-cooling, m-chloroperbenzoic acid (purity 80%, 1.23 g) is added. The mixture is stirred at room temperature for 8.5 hours. The reaction mixture is then washed with aqueous sodium thiosulfate, aqueous sodium hydrogen carbonate, dilute HCl and aqueous sodium chloride in the order mentioned, dried over magnesium sulfate, and concentrated under reduced pressure. The resultant crude crystals are washed with ether to give diphenylmethyl 3-acetoxymethyl-7-methoxyimino-3-cephem-4-carboxylate 1,1-dioxide (0.65 g).

mp 176°–178.5° C.

IR(nujol) 1790, 1735 cm$^{-1}$

NMR(CDCl$_3$)δ 1.99(s, 3H), 3.88(m, 2H), 4.13(s, 3H), 4.85(ABq, J=16 Hz, 2H), 5.30(s, 1H), 6.95(s, 1H), 7.35(s, 10H)

What we claim is:

1. A method of producing a compound of the formula:

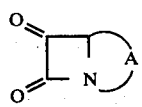 (I)

wherein A is a group of the formula:

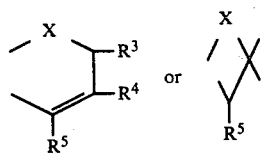

in which

R³ is hydrogen or alkyl,

R⁴ is hydrogen, halogen, alkyl, alkoxy, alkanoyloxymethyl, alkoxycarbonyloxymethyl, alkanesulfonyloxymethyl, carbamoyloxymethyl, mono-, di- or trihaloalkanoyl carbamoyloxymethyl, aroyloxymethyl, ar (lower) alkanoyloxymethyl, aryloxycarbonyloxymethyl, aryloxy (lower) alkanoyloxymethyl, arylglyoxyloyloxymethyl, arenesulfonyloxymethyl, heterocyclic carbonyloxymethyl, heterocyclic (lower) alkanoyloxymethyl, heterocyclic glyoxyloyloxymethyl, or heterocyclic-thiomethyl comprising as the heterocyclic moiety unsaturated 3 to 8 membered monocyclic heterocyclic containing 1 to 4 nitrogen atoms, saturated 3 to 8 membered monocyclic heterocyclic containing 1 to 4 nitrogen atoms, unsaturated fused heterocyclic containing 1 to 4 nitrogen atoms, unsaturated 3 to 8 membered monocyclic heterocyclic containing 1 to 2 oxygen atoms and 1 to 3 nitrogen atoms, saturated 3 to 8 membered monocyclic heterocyclic containing 1 to 2 oxygen atoms and 1 to 3 nitrogen atoms, unsaturated fused heterocyclic containing 1 to 2 oxygen atoms and 1 to 3 nitrogen atoms, unsaturated 3 to 8 membered monocyclic heterocyclic containing 1 to 2 sulfur atoms and 1 to 3 nitrogen atoms, saturated 3 to 8 membered monocyclic heterocyclic containing 1 to 2 sulfur atoms and 1 to 3 nitrogen atoms, unsaturated 3 to 8 membered monocyclic heterocyclic containing 1 to 2 sulfur atoms, unsaturated fused heterocyclic containing 1 to 2 sulfur atoms and 1 to 3 nitrogen atoms, unsaturated 3 to 8 membered monocyclic heterocyclic containing an oxygen atom, unsaturated 3 to 8 membered monocyclic heterocyclic containing an oxygen atom and 1 to 2 sulfur atoms, unsaturated fused heterocyclic containing 1 to 2 sulfur atoms, unsaturated fused heterocyclic containing an oxygen atom and 1 to 2 sulfur atoms, and said heterocyclic moieties substituted with 1 to 5 substituents comprising lower alkyl, lower alkoxy, lower alkylthio, lower alkylamino, cyclo (lower) alkyl, cyclo (lower) alkenyl, hydroxy, halogen, amino, cyano, nitro, carboxy and protected carboxy, R⁵ is carboxy or protected carboxy, and X is —S— or —O—, or a salt thereof or a hydrate thereof, which comprises reacting a compound of the formula:

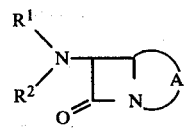 (II)

wherein

R¹ is trihalomethanesulfonyl,

R² is trihalomethanesulfonyl, alkanoyl, alkoxycarbonyl, alkanesulfonyl, carbamoyl, mono-, di- or trihaloalkanoyl carbamoyl, aroyl, ar (lower) alkanoyl, aryloxycarbonyl, aryloxy (lower) alkanoyl, arylglyoxyloyl, arenesulfonyl, heterocyclic carbonyl, heterocyclic (lower) alkanoyl, or heterocyclic glyoxyloyl, and A is as defined above, or a salt thereof, with an inorganic or organic base, and then subjecting the resultant compound to hydrolysis in the presence of an acid.

2. A method of producing a compound of the formula:

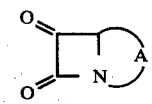 (I)

wherein A is a group of the formula:

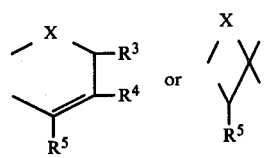

in which

R³ is hydrogen or alkyl,

R⁴ is hydrogen, halogen, alkyl, alkoxy, alkanoyloxymethyl, alkoxycarbonyloxymethyl, alkanesulfonyloxymethyl, carbamoyloxymethyl, mono-, di- or trihaloalkanoyl carbamoyloxymethyl, aroyloxymethyl, ar (lower) alkanoyloxymethyl, aryloxycarbonyloxymethyl, aryloxy (lower) alkanoyloxymethyl, arylglyoxyloyloxymethyl, arenesulfonyloxymethyl, heterocyclic carbonyloxymethyl, heterocyclic (lower) alkanoyloxymethyl, heterocyclic glyoxyloyloxymethyl, or heterocyclic-thiomethyl comprising as the heterocyclic moiety unsaturated 3 to 8 membered monocyclic heterocyclic containing 1 to 4 nitrogen atoms, saturated 3 to 8 membered monocyclic heterocyclic containing 1 to 4 nitrogen atoms, unsaturated fused heterocyclic containing 1 to 4 nitrogen atoms, unsaturated 3 to 8 membered monocyclic heterocyclic containing 1 to 2 oxygen atoms and 1 to 3 nitrogen atoms, saturated 3 to 8 membered monocyclic heterocyclic containing 1 to 2 oxygen atoms and 1 to 3 nitrogen atoms, unsaturated fused heterocyclic containing 1 to 2 oxygen atoms and 1 to 3 nitrogen atoms, unsaturated 3 to 8 membered monocyclic heterocyclic containing 1 to 2 sulfur atoms and 1 to 3 nitrogen atoms, saturated 3 to 8 membered monocyclic heterocyclic containing 1 to 2 sulfur atoms and 1 to 3 nitrogen atoms, unsaturated 3 to 8 membered monocyclic heterocyclic containing 1 to 2 sulfur atoms, unsaturated fused heterocyclic containing 1 to 2 sulfur atoms and 1 to 3 nitrogen atoms, unsaturated 3 to 8 membered monocyclic heterocyclic containing an oxygen atom, unsaturated 3 to 8 membered monocyclic heterocyclic containing an oxygen atom and 1 to 2 sulfur atoms, unsaturated fused heterocyclic containing 1 to 2 sulfur atoms, unsaturated fused heterocyclic containing an oxygen atom and 1 to 2 sulfur atoms, and said heterocyclic moieties substituted with 1 to 5 substituents comprising lower alkyl, lower alkoxy, lower alkylthio, lower alkylamino, cyclo (lower) alkyl, cyclo (lower) alkenyl, hydroxy, halogen, amino, cyano, nitro, carboxy and protected carboxy, $R^5$ is carboxy or protected carboxy, and X is —S— or —O—, or a salt thereof or a hydrate thereof, which comprises reacting a compound of the formula:

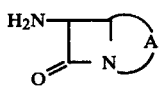 (IV)

wherein A is as defined above, or a reactive derivative at the amino group thereof comprising a silyl, isocyanate, isothiocyanate or Schiff base derivative, or a salt thereof, with a trihalomethanesulfonylating agent comprising trihalomethanesulfonic acid, its acid halide or acid anhydride, and then an acylating agent comprising an organic carboxylic acid or organic sulfonic acid or reactive derivative thereof capable of introducing the grouping defined in $R^2$, or alternatively with said acylating agent and then said trihalomethanesulfonylating agent, and further reacting the resultant compound of the formula:

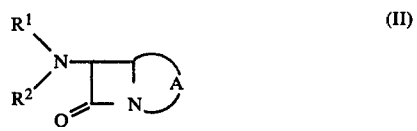 (II)

wherein $R^1$ is trihalomethanesulfonyl, $R^2$ is trihalomethanesulfonyl, alkanoyl, alkoxycarbonyl, alkanesulfonyl, carbamoyl, mono-, di- or trihaloalkanoyl carbamoyl, aroyl, ar (lower) alkanoyl, aryloxycarbonyl, aryloxy (lower) alkanoyl, arylglyoxyloyl, arenesulfonyl, heterocyclic carbonyl, heterocyclic (lower) alkanoyl, or heterocyclic glyoxyloyl, and A is as defined above, or a salt thereof, with an inorganic or organic base, and then subjecting the resultant compound to hydrolysis in the presence of an acid.

* * * * *